United States Patent [19]
Jimenez et al.

[11] 4,367,752
[45] Jan. 11, 1983

[54] APPARATUS FOR TESTING PHYSICAL CONDITION OF A SUBJECT

[75] Inventors: Oscar Jimenez, Miami; Frank J. Bianco, Pembroke Pines, both of Fla.

[73] Assignee: Biotechnology, Inc., Miami, Fla.

[21] Appl. No.: 145,765

[22] Filed: Apr. 30, 1980

[51] Int. Cl.³ ............................................. A61B 5/02
[52] U.S. Cl. ................... 128/689; 128/706; 128/707; 128/782
[58] Field of Search ............ 128/668, 670–672, 128/639, 644, 687–691, 706–707, 702–704, 718, 779, 782; 364/410, 413, 415, 417

[56] References Cited

U.S. PATENT DOCUMENTS

| | | | |
|---|---|---|---|
| 3,395,698 | 8/1968 | Morehouse | 128/707 |
| 3,518,985 | 7/1970 | Quinton | 128/707 |
| 3,534,727 | 10/1970 | Roman | 128/644 |
| 3,675,640 | 7/1972 | Gatts | 128/671 |
| 3,826,246 | 7/1974 | Paddi et al. | 128/644 X |
| 3,978,849 | 9/1976 | Geneen | 128/690 |
| 4,053,951 | 10/1977 | Hudspeth et al. | 128/670 |
| 4,101,071 | 7/1978 | Brejnik et al. | 128/687 |
| 4,108,166 | 8/1978 | Schmid | 128/706 |
| 4,112,928 | 9/1978 | Putsch | 128/707 |
| 4,144,568 | 3/1979 | Hiller et al. | 364/410 |
| 4,181,135 | 1/1980 | Andresen et al. | 128/702 X |
| 4,192,000 | 4/1980 | Lipsey | 364/415 |
| 4,202,350 | 5/1980 | Walton | 128/690 |
| 4,216,956 | 8/1980 | Yamamura et al. | 272/70 |
| 4,220,996 | 9/1980 | Searcy | 364/561 |
| 4,223,211 | 9/1980 | Allsen et al. | 235/92 DN |

OTHER PUBLICATIONS

Kato, S. et al., "Application of Micro-Computer to Integrated Sleep Monitor", Euromicro (Netherlands) V3, #4, Oct. 1927.

Primary Examiner—Kyle L. Howell
Assistant Examiner—Francis J. Jaworski
Attorney, Agent, or Firm—Lowe, King, Price & Becker

[57] ABSTRACT

The physical condition of a subject is tested by a transducer mounted on the subject which derives a first signal indicative of heart activity. An electronic instrument housing carried by the subject includes terminals responsive to the first signal and (a) an inertial member for monitoring the quantity of repetitive actions taken by a limb of the subject and for deriving a second signal indicative of the quantity, (b) a keyboard for enabling signals to be derived indicative of numerical quantities associated with plural physiological parameters of the subject, (c) a clock source for deriving timing signals, (d) a digital computer responsive to the first, second, timing and keyboard signals for deriving plural digital output signals indicative of different physical activities of the tested subject, (e) a visual digital indicator, (f) plural key switches, each associated with a different one of the physical activities, and (g) circuitry responsive to activation of the plural key switches for selectively coupling different ones of the plural output signals to the visual indicator so only one of the output signals is supplied to the indicator at a time.

53 Claims, 15 Drawing Figures

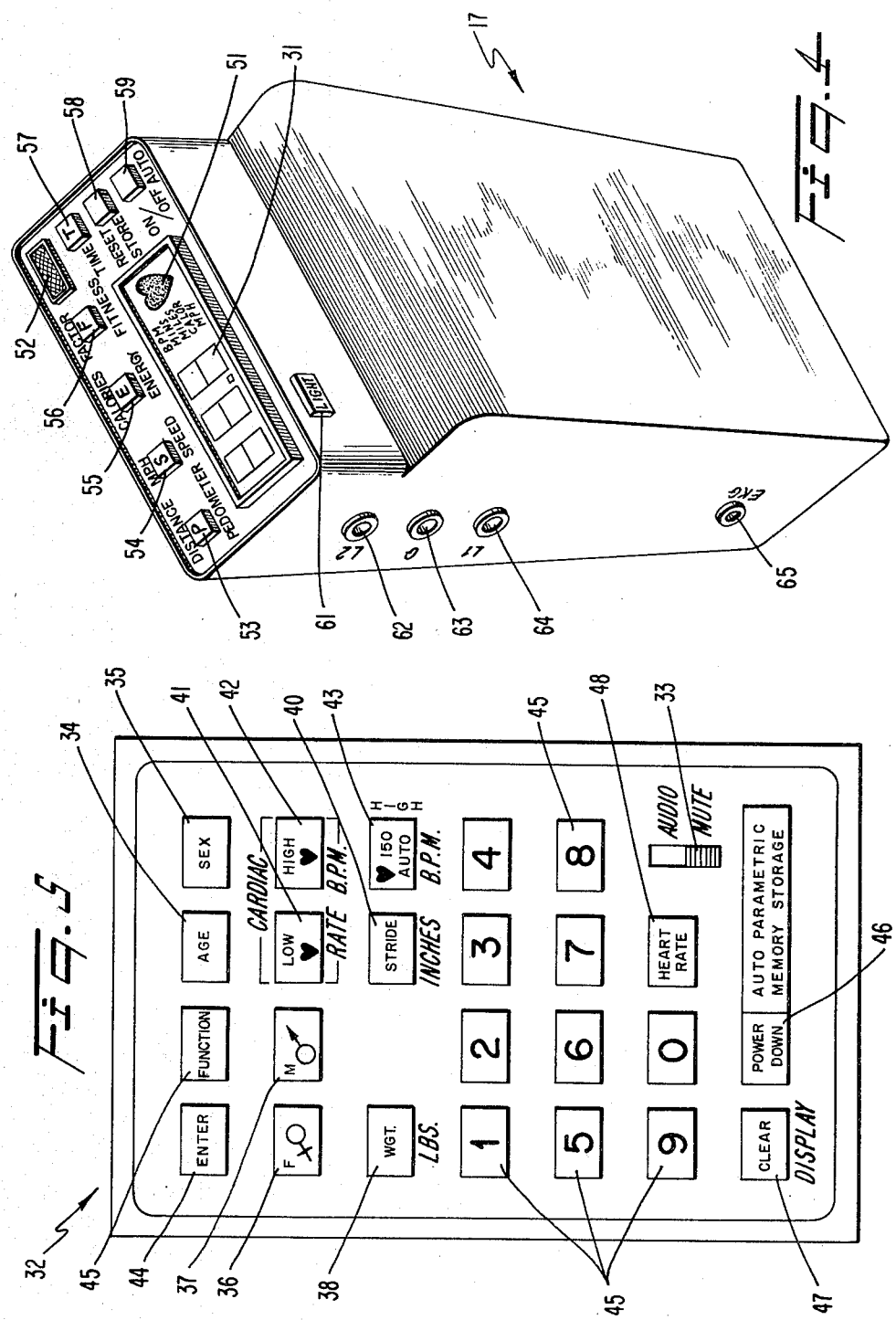

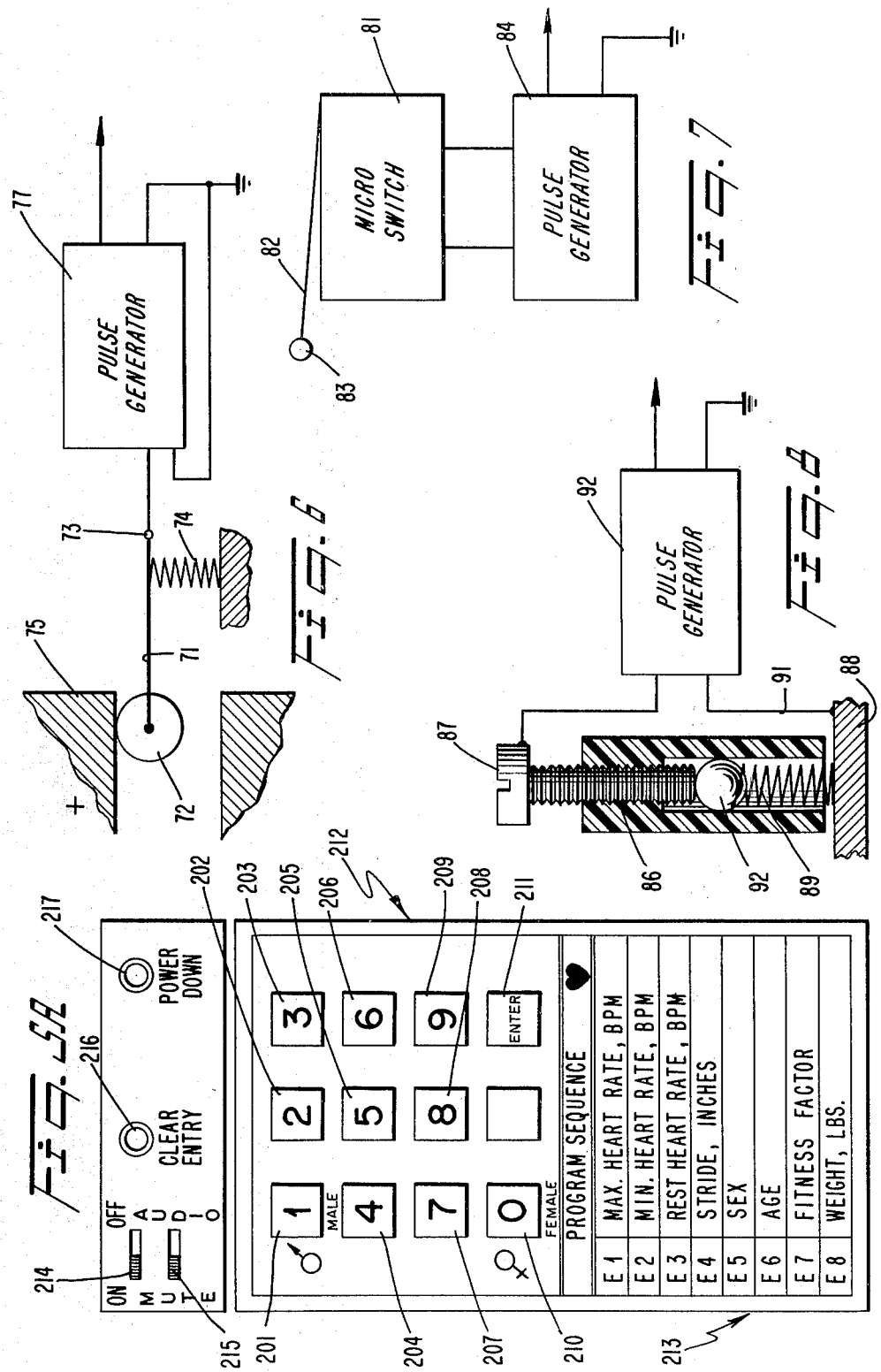

APPARATUS FOR TESTING PHYSICAL CONDITION OF A SUBJECT

TECHNICAL FIELD

The present invention relates generally to apparatus for testing the physical condition of a subject and, more particularly, to an apparatus for testing the physical condition of a subject in response to signals indicative of heart activity of the subject and of the distance traversed by a limb of the subject during a timed testing period to provide a fitness indication of the cardiovascular system of the subject and/or parametric data related to exercise.

BACKGROUND ART

Numerous devices have been devised, and some actually employed, for testing the physical condition of a human subject. The devices are employed for medical purposes, as well as to apprise an athlete of his physical condition during training. In a typical medical device, utilized in stress tests for physiological purposes, an electrocardiogram of a subject being tested is continuously taken. In addition, blood pressure is intermittently monitored, and in some instances respiration rate is measured. The oxygen transfer to the lungs of the subject is also measured. Other devices have been developed wherein elapsed time of a test is combined with heart beat pulses to derive an indication of a heart beat rate, as well as caloric consumption and total calories expended. Other devices which base calorie consumption only on heart rate are quite inaccurate because they do not take into consideration data required to calculate calorie consumption in accordance with variables which are known to effect calorie consumption viz: distance traveled, length of exercise time, resting heart rate, resting and exercise heart rate, weight of subject, change in heart rate in MET (multiples of metabolic need for sitting quietly) and oxygen consumed per minute per pound. Other systems have been devised wherein physical exertion parameters of a subject are determined as a function of the age of a subject, in combination with heart pulse frequency, to determine the stress on the heart.

Other devices have been proposed for monitoring physical condition of a subject in response to a signal derived from an electromechanical sensor adapted to generate an electrical pulse in response to each step taken by an individual while walking, running or jogging. In one particular system of this type, a computer counts the number of steps taken by the subject and, in response to a timing signal from a clock source, measures the rate at which the steps are taken. The computer continuously integrates the number of steps taken multiplied by the step rate over a time interval while the subject is being tested. The computer supplies signals to aural and visual outputs, to provide indications of the physical condition of the subject, and to apprise the subject as to whether he is achieving or exceeding predetermined levels associated with his physical parameters.

These prior art devices are frequently based upon information derived from two books written by Dr. Kenneth H. Cooper entitled "Aerobics", M. Evans and Company, Inc., New York, N.Y. (1968) and "The New Aerobics", M. Evans and Company, Inc., New York, N.Y. (1970). Dr. Cooper, in these books, defines the word aerobics as exercises that increase the supply of oxygen to various parts of the body of a subject. Exercises which typically fall into the category of aerobics are walking, jogging, running, hiking, climbing, tennis, cycling, weight lifting and swimming. Diligent pursuit of any of these exercises results in improved physical condition of a subject.

As previously indicated, the previously developed devices provide an indication of physical condition by relying primarily upon one of two variables, namely heart rate during exercise or distance traveled by a limb in exercise. Because heart rate is a prime indicator of physical stress, it is valuable to constantly monitor heart rate during exercise of a subject. Maximum heart rate in human subjects is dependent on age. Clinical evidence exists to indicate that optimum benefit from aerobic exercise is obtained when the cardiovascular system of the subject is exercised at a target heart rate range of between 75% to 85% of maximum heart rate for a particular subject for at least twelve minutes. However, clinical evidence developed by Dr. Azorides R. Morales, reported in September 1979, Medical World News, pps. 37 and 38, also exists to indicate that certain individuals, due to physical defects or condition, cannot use the standard 75% to 85% of maximum heart rate for their age, to calculate the target rate, without risk of heart damage to the subject. Certain of the prior art devices rely almost exclusively upon the heart rate monitoring to provide an indication of the physical condition of the subject. The other class of devices relies upon a measurement of distance and rate of distance covered to indicate the physical condition of the subject. These two classes of devices, however, have not generally provided the subject or physician with a complete analysis of the physical condition of a subject.

DISCLOSURE OF THE INVENTION

In accordance with a basic concept of the present invention, parameters concerning physiological parameters of an exercising subject, e.g. the physical condition and calorie consumption of the subject, are tested by monitoring heart activity of the subject during an exercise period and the distance traversed by a limb of the subject during testing. A computer means responds to the heart activity and distance traversed signals, as well as a timing signal from a clock source and a signal indicative of at least one predetermined constant physiological parameter of the subject, to derive a signal indicative of the physical activity of the subject being tested. An indicator responds to the physical activity signal to provide visual and/or aural signals to a subject or physician.

In the preferred embodiment, the physiological parameters determined by the computer are, heart rate, speed of the subject, fitness, and calories consumed of the exercise. Distance is determined directly from indications of number of cycles the limb moves and a known, i.e., constant, predetermined physiological input parameter relating each cycle of limb movement to traversed distance; for a runner or walker the number of strides is counted and the stride length is the known input. From measurements of elapsed time and distance traveled, speed is calculated. Fitness is computed from distance traveled over a relatively long interval, e.g. 12 minutes, of maximum exercise, based on data published in Cooper's books, and is therefore a measure of oxygen uptake by the subject. Calorie consumption is computed in response to exercise, weight of the subject, sex of the subject, the change in heart rate per MET (multiples of metabolic need for sitting quietly) and the milliliters of oxygen consumed by the subject per minute per pound of the subject. Resting heart rate is set into the computer from measurements on the subject at the time of awakening, while exercising heart rate is measured continually during the exercise. Heart beats per MET and oxygen per minute per pound are determined from a calculation by the computer as being directly proportional to computed fitness or from table look-ups stored in a memory of the computer or from printed tables. If fitness has not been previously computed, it can also be determined from a printed table. All data derived from printed tables can be entered into the computer.

In one embodiment, the heart activity of the subject is indicated by monitoring the number of heartbeats of the subject. Preferably, the heart beats are detected by electrodes on the subject which derive an electrocardiogram signal. As is well known, an electrocardiogram signal includes several pulses referred to as p, q, r, s and t pulses, all of which are derived each time the heart beats. The r pulse has a relatively large magnitude, considerably larger than the remaining pulses, and is detected in a preferred embodiment of the invention to indicate the number of heart beats. The r pulses are detected by a band pass filter which passes the r pulses and feeds the passed r pulses to a clamping circuit for the peaks of the r pulses. A full wave rectifier is provided for the r pulses so that r pulses of only one polarity are applied to the clamping means, regardless of connections of the electrodes to the r pulse detecting circuitry. To prevent possible high amplitude artifact noise in the electrocardiogram signal from being erroneously detected as r pulses, the heart activity signal is not coupled to the computer in response to a pair of adjacent detected r pulses occurring in less than a predetermined interval which is less than the possible period between adjacent beats of a heart of a subject.

In a preferred embodiment, three electrodes are provided on the subject and are carried by a garment that presses the electrodes against the skin of the subject. The garment may be a chest strap, or in the case of a female athlete, a brassiere. One of the electrodes is adapted to abut on skin against the rib cage, in the vicinity of the heart of the subject, a second of the electrodes is adapted to abut on skin against the sternum of the subject, while a third electrode is adapted to abut on skin just below the right chest quadrant of the subject.

To provide a low electrical conductance path between the skin of the subject and the electrodes for the electrocardiogram signals generated by the subject, each of the electrodes includes a highly electrically conductive gel which adheres to the skin of the subject while moistened. Moistening of the gel can occur by applying water from an external source, or in response to perspiration from the subject. In a preferred embodiment, the gel includes karaya gum and glycerin.

Associated with each electrode is a lead wire and a shield for the lead wire or a common shield for all of the lead wires. Because the three lead wires and the shield are connected to three sets of input terminals of an electronic instrument housing, there is a tendency for the grounded shield voltage to vary relative to ground of the housing. To obviate this problem, a common mode rejection circuit includes a ground terminal for the lead of one of the electrodes. The lead wires for the other two electrodes are connected to a differential amplifier arrangement. In the preferred configuration, the differential amplifier means includes a buffer amplifier for the voltages applied to the two leads and a differential amplifier responsive to the output voltages of the two buffer amplifiers. The differential amplifier is referenced to ground to provide the common mode rejection for voltages generated by the electrodes.

An alternative arrangement for monitoring heart beats employs photo-plethysmography wherein infra red absorption properties by capillaries in the skin of the subject are monitored by an infra red source and detector. The detector derives a pulse for each heart beat and avoids the necessity for a harness carrying electrodes and the accompanying circuitry.

The visual indicator is preferably a liquid crystal display (LCD) or a light emitting diode (LED) display for digital numeral indicating signals derived by the computer. Different signals are applied to the visual indicator on a selective basis to enable the subject and/or physician to be apprised of various aspects of the physical condition of the subject. If the subject is running, walking, or jogging, the signal indicative of distance traversed by a limb of the subject is derived by a pedometer. In this case, the indicator is selectively responsive to signals indicative of heart beats per minute, elapsed time of the exercise interval, the distance traversed by the subject, the number of calories used by the subject during the interval, the rate of speed of the subject during the interval, and a fitness factor which is a function of maximum oxygen uptake. The distance transversed, consumption of calories and fitness factor are calculated by the computer in response to entry on a keyboard of the physiological parameters of sex, age, resting heart rate, weight, and stride of the subject.

The aural indicator signals heart beat rate to the subject in response to entry on the keyboard of minimum heart rate and can provide the subject with an indication that he is exercising at an excessive rate in response to entry on the keyboard of maximum heart rate. In particular, the aural indicator is pulsed in response to each heart beat when the computer is responsive to at least a predetermined number of heart beats in a predetermined interval. The aural indicator is continuously activated in response to the heart beat rate exceeding a predetermined level, as indicated by the computer means.

In accordance with a further feature of the invention, the computer means includes a memory that is supplied with signals indicative of the predetermined, constant physiological parameters. By activating a power down key on the keyboard the memory continues to store the signals indicative of the predetermined, constant physiological parameters even when a DC power supply for each of the computer means, signal deriving means and indicator means is decoupled from the remainder of the computer means, as well as signal deriving means and indicator means. It is, however, possible to supply new signals to the computer memory indicative of the predetermined, constant physiological parameters of the subject, as desired.

In a preferred configuration, the signal deriving means, visual and aural indicators, computer means and pedometer are all located in an electronic instrument housing adapted to be mounted on the subject. The electronic instrument housing includes a keyboard for enabling derivation of signals indicative of numerical quantities associated with a plurality of physiological parameters of the subject, as well as plural key switches, each associated with a different one of the physical activities. Thus, the electronic instrument housing contains all of the structure, except for the electrodes, necessary to provide the subject and/or physician with an indication of the physical condition of the subject. The instrument housing can be connected by a jack to a conventional EKG monitoring device.

It is, accordingly, an object of the present invention to provide a new and improved apparatus for testing the physical condition of a human subject.

An additional object of the invention is to provide a new and improved apparatus for indicating physical condition of a subject in response to signals indicative of heart activity of the subject and distance traversed by a limb of a subject during testing.

Another object of the invention is to provide a new and improved programmable apparatus for testing the physical condition of a subject, which apparatus can be worn on the subject and provide the subject and/or others with visual and aural indications of his physical condition and whether he is exceeding his physical capabilities.

Still another object of the invention is to provide a portable apparatus which can be worn by a jogger, walker, hiker, or runner, which apparatus provides the subject with an indication of his heart beat per minute, miles traversed, speed of traversal, length of exercise period, calorie consumption, and, upon completion of 12 minutes of maximum activity, his fitness based on maximum oxygen uptake.

The above and still further objects, features and advantages of the present invention will become apparent upon consideration of the following detailed description of several specific embodiments thereof, especially when taken in consideration with the accompanying drawings.

BRIEF DESCRIPTION OF THE DRAWINGS

FIG. 4 is a generally front, perspective view of an electronic instrument housing for a portion of the apparatus of the present invention;

FIGS. 5 and 5a are back views of alternative embodiments of the instrument housing illustrated in FIG. 4;

FIGS. 6, 7 and 8 are illustrations of various pedometers that can be mounted in the housing of FIGS. 4 and 5;

Figure 1:
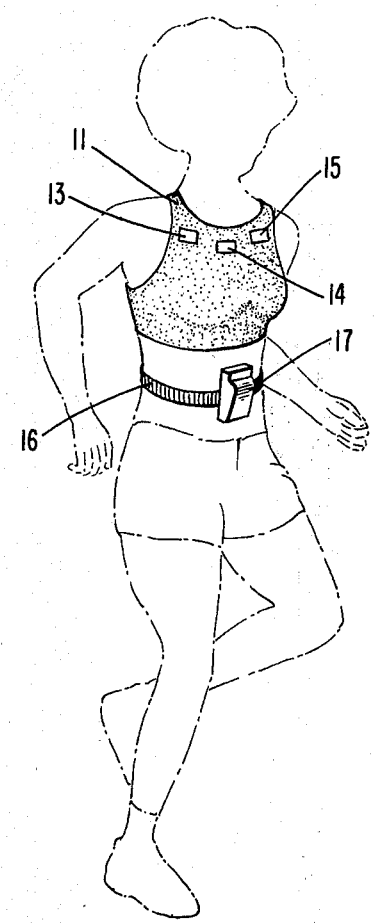
FIG. 1 is an illustration of a female jogger, runner, hiker or walker equipped with the apparatus of the present invention.
Figure 2:
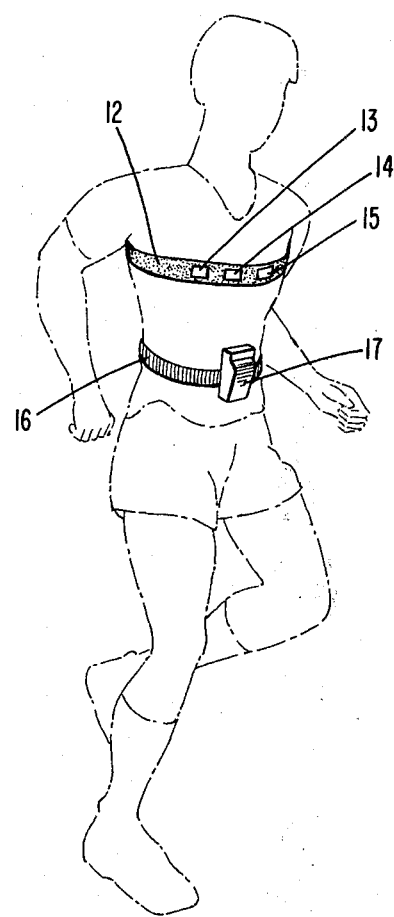
FIG. 2 is a diagram of a male jogger, runner, hiker or walker equipped with the apparatus of the present invention.

BEST MODE FOR CARRYING OUT THE INVENTION:

Reference is now made to FIGS. 1 and 2 wherein there are respectively illustrated female and male athletes equipped with the present invention. The female and male athletes respectively wear garments 11 and 12, each carrying three electrodes 13–15 which are pressed by the garments against the skin of the athlete. Each athlete also wears a waist band which carries electronic instrument housing 17, connected to the electrodes by a suitable cable or lead wire arrangement. For the female athlete, the garment is a brassiere 11, preferably of the type known as a "running bra" which minimizes breast bouncing, skin irritation and collagen tissue breakdown of the breasts. For the male athlete, the garment is a chest strap 12, worn slightly above the vicinity of the male breast. Each of garments 11 and 12 carries three electrodes 13, 14 and 15 which are electrically connected to the skin of the athlete, i.e., subject being tested for physical condition, to supply electrocardiogram voltages generated by the subject to leads which extend to electronic instrument housing 17, which is mounted on the waist band. Each of brassiere 11 and chest strap 12 is provided with a fastener which firmly secures the brassiere or chest strap to the chest of the subject so that electrode 13 abuts on skin just below the right chest quadrant of the subject, electrode 14 abuts on skin against the sternum of the subject, in the center of the chest of the subject, and electrode 15 abuts on skin against the rib cage, in the vicinity of the heart of the subject.

Figure 3:
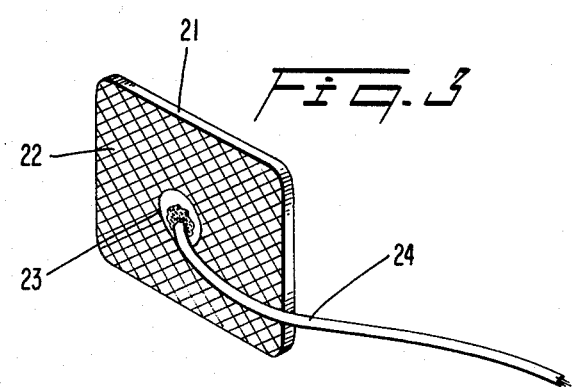
FIG. 3 is a perspective view of electrodes mounted in garments worn by the test subjects of FIGS. 1 or 2.

A preferred configuration for each of electrodes 13–15 is illustrated in FIG. 3 and includes a generally square layer 21 of a gel which is highly electrically conductive and adheres to the skin of the subject while moistened. Layer 21 is illustrated as being of generally square configuration, but is is to be understood that it can take any suitable geometry, having sufficient contact area on a face adapted to contact the skin of the subject. On the face of layer 21 opposite from the face adapted to contact the skin of the subject is a metal mesh layer 22 of stainless steel or soft annealed brass carrying an impreganted film of silver-silver chloride. Layer 22 includes a central button 23 which is secured to lead wire 24 of a shielded or unshielded cable that is connected to a reference potential (preferably zero or ground voltage) within instrument housing 17. Lead wire 24 for each of electrodes 13–15 has its own separate shield in one embodiment, or, in another embodiment, the lead wires for the various electrodes have a common shield in a single cable; however the latter configuration may have deleterious results due to cross coupling of signals transduced by electrodes 13–15.

In a preferred configuration, gel layer 21 is composed of the following ingredients:

Karaya gum, a hydrophilic gum which is carbohydrate polymer exuded from certain Indian trees of the genus sterculia, 33 percent by weight;
Glycerin, 60 percent by weight;
Ethanol, 1 percent by weight;
Methyl-p-hydroxybenzoate, 0.01 percent by weight;
Propyl-p-hydroxybenzoate, 0.01 percent by weight;
Sodium chloride, 4 percent by weight;
Potassium chloride, 2 percent by weight.

The Karaya gum forms a highly electrically conductive translucent colloidal gel when mixed with the remaining ingredients. Layer 21 has an area of approximately four centimeters by four centimeters, and a two millimeter thickness. If desired or necessary, layers 21 are moistened with water or a saline solution prior to the subject securing brassiere 11 or chest strap 12 in place. Alternatively, layer 21 can remain dry prior to installation and can be moistened by perspiration from the skin of the subject.

It is to be understood that other electrodes can be utilized in lieu of the electrodes specifically illustrated in FIG. 3. In particular, an In-Vivo Metric Systems type E221 electrode or a Beckman Instruments Company type 650437 electrode could be employed. If either of these electrodes is employed, however, an electrolyte gel must be employed to provide proper coupling of the electrocardiogram voltage to lead 24.

Reference is now made to FIGS. 4 and 5 of the drawings wherein there is illustrated the exterior of electronic instrument housing 17 which is carried on waist band 16. Inside of housing 17 is located electronic circuitry which is reponsive to signals derived from electrodes 13-15, an instrument for deriving a signal indicative of the distance traversed by a limb of the subject being tested (generally a pedometer which counts the number of strides taken by the subject), a clock source for deriving a timing signal, and digital computer means responsive to the electrode signals, the distance traversed signal, the timing signal, as well as predetermined physiological parameters of the subject. The computer means derives a signal which is indicative of the physical activity of the subject being tested and supplies the signal to an indicator, in the form of a liquid crystal digital display 31 mounted on the top face of housing 17. Housing 17 is shaped generally as a right parallelepiped, having approximately a six inch length, three inch width, and one inch thickness.

Physiological data concerning the subject being tested are entered into the computer means with keyboard 32 on the back face of housing 17, i.e., the face of the housing which is remote from the body of the subject being tested. Keyboard 32 includes a matrix of keys which enable differing predetermined, constant physiological parameters and differing numbers relative to some of these parameters to be entered into the computer. Other keys and slide switch 33 are provided for functions associated with the types of indications (aural and/or visual) which are provided by housing 17 and data storage in a memory of the computer means included in the housing. The predetermined, constant physiological functions which can be entered are age, sex, male, female, weight, fitness factor, and stride of the subject, entries respectively associated with keys 34, 35, 36, 37, 38 and 40. In addition, keys 41 and 42 are respectively associated with resting heart rate, low and high heart rates, in beats per minute, for the subject, as determined from a chart which is supplied to the tested subject or to a physician. Key 43 is for entry of a maximum beat rate of 150 beats per minute, which has been clinically found to be a maximum heart rate for a significant (25%) of the population having a congenital heart defect.

In general, an entry is made by depressing function key 45, then pressing a physiological key and keys associated with the particular physiological factor (e.g., 0-9 numeral keys 45 or a specific sex key 36 or 37), in turn followed by pressing enter key 44. For example, if the subject is known to have the congenital heart defect, function key 45 is pressed, followed by pressing of key 43, in turn followed by pressing of enter key 44. After depression of function key 45 and sex key 35, one of male or female keys 36 or 37 is pressed, in turn followed by depression of enter key 44. After depression of function key 45 and one of keys 34 or 38-42, a numerical value is entered by depressing one or more of 0-9 numeral keys 45, which is followed by depressing enter key 44.

Keyboard 32 includes three additional keys 46, 47 and 48, respectively labeled "power down", "clear" and "heart rate". Depression of "power down" key enables the physiological parameters associated with the subject to be stored in the memory of the computer means within housing 17 indefinitely, even when power is decoupled from the remainder of the unit. If the physiological parameters of the subject change or the device is used for a different subject, new parameters can be entered into the memory merely by pressing function key 45, the desired physiological key, the specific sex or numerical value keys, and enter key 44. Clear key 47 is depressed when it is desired to remove all entries from keyboard 32 and to clear display 31. Heart rate key 48 is depressed by the subject while he is in a rest condition and after brassiere 11 or chest strap 12 has been secured in place and leads 24 of electrodes 13-15 have been connected to input terminals of instrument housing 17.

On the top face of instrument housing 17, in addition to liquid crystal digital display 31, are a liquid crystal display 51, in the form of a heart, and a cloth or other air pervious screen 52, which allows aural pulses and continuous aural tones to be coupled exteriorly of housing 17. Liquid crystal display 51 is activated at the same rate as heart beats of the subject. With slide switch 33 in the upper, "audio" position, an aural pulsed tone is coupled through screen 52 each time the heart of the subject beats, when the heart beat rate is greater than the rate which is entered after depression of low rate key 41. A continuous aural tone is coupled through screen 52 in response to the heart beat rate of the subject exceeding a predetermined maximum, associated with entry of a numeral value, subsequent to depression of high rate key 42 or 150 rate key 43. The subject is advised to reduce his activity if he hears the continuous tone.

On the upper face of housing 17 are 8 additional keys 53-60, respectively associated with the output functions: distance traversed (P key 53), average speed (S key 54), calories or energy consumed (E key 55), fitness factor (F key 56), elapsed time of exercise (M key 57), stop time of exercise/store (SP key 58), beats/minute (key 59), and start time of exercise (ST key 60). In response to depression of stop time of exercise/store key 58, followed by depression of one of keys 53-57, digital display 31 is activated to indicate the numerical value associated with the depressed key. Display 31 is supplied by the digital computer means in instrument housing 17 with a signal derived directly from the pedometer and the stride length input from keyboard 32 in response to depression of keys 58 and 53. In response to depression of keys 58 and 54, the computer means in instrument housing 17 responds to signals in the memory thereof indicative of the calculated distance and elapsed time to supply display 31 with a signal indicative of the speed of the subject while running, jogging, walking or hiking. In response to depression of keys 58 and 55, the computer responds to the signals from electrodes 13-15 and the elapsed time and distance signals to supply display 31 with an indication of the number of calories consumed by the subject during the exercise interval. In response to depression of keys 58 and 56, the computer again responds to the signals from electrodes 13-15 and the calculated values of distance and elapsed time to provide an indication of maximum oxygen uptake, which is correlated with a fitness factor for the subject.

At the beginning of the exercise routine, stop/store key 58 is depressed and then start key 60 is depressed to initiate operation of the timing signal within the computer. During the exercise routine, any of the parameters, except the fitness factor, can be determined by depressing one of keys 53-55 or 57, e.g., the elapsed time of the exercise period is determined by depressing M key 57. After the exercise routine has been completed, stop/store key 58 is depressed once to decouple signals from the pedometer and electrocardiogram electrodes, as well as to decouple the timing signal from the computer means. Thereafter, any of keys 53-57 can be depressed to enable the desired information to be observed from display 31. After the exercise routine has been completed and all of the desired variables have been read from display 31, power down key 46 is depressed causing the calculated and input parameters to remain in memory indefinitely while decoupling power from the aural signal source and displays 31 and 51. If data storage is not desired, on/off key 59 is depressed to remove power from the memory and inactivate displays 31 and 51, as well as to prevent the derivation of aural signals.

If a liquid crystal display is provided, display 31 is energized immediately in response to depression of any of keys 53-57. If the device is used at night, liquid crystal displays 31 and 51 are illuminated by light emitting diode 61, on the front face of housing 17, immediately below display 31, in response to depression of any of keys 53-57.

On one of the side walls of instrument housing 17 are located jacks 62, 63 and 64 for the shielded cables surrounding leads 24 which are connected to electrodes 13-15. Alternatively, jacks 62-64 can be replaced with a single female connector that is adapted to receive prongs of a male connector in a single cable which connects electrodes 13-15 to electronic circuitry within instrument housing 17. Below jacks 62-64 is a further jack 65 which enables an EKG signal picked up by electrodes 13-15 to be supplied to a conventional electrocardiogram paper tape recorder.

Reference is now made to FIG. 5A of the drawing wherein there is illustrated a second embodiment of instrument housing 17. In the embodiment of FIG. 5a, the number of keys is reduced compared to the number of keys in the embodiment of FIG. 5. Key activation is associated with and directed in response to command indicia supplied to display 31. In response to the indicia of display 31 having certain values, the operator of the keyboard illustrated in FIG. 5a makes certain entries, as directed by printed table 213 positioned below keys 201-211 of keyboard 212.

Keyboard 212 includes 10 numerical keys 201 209 and 210, respectively provided for the numerals 1-9 and 0. Keys 201 and 210, in addition to being associated with the numerals 1 and 0, are function keys for entry of male and female gender of the subject being tested. A further key 211, for enabling entry of numbers and functions associated with the remaining keys, is also provided.

In the embodiment of FIG. 5a immediately above keyboard 212, are additional keys 214-217 associated with various functions. In particular, there is an on-off toggle switch 214, as well as a mute-audio toggle switch 215, which enables activation and deactivation of the aural signals derived from the speaker behind screen 52. To the right of switches 214 and 215 are keys 216 and 217, respectively provided for clearing entries into keyboard 212 and the power down operation which enables the memory in the computer to store information indefinitely without power being supplied to visual indicators 31 and 51, as well as the aural signal source.

In use, toggle switch 214 is slid to the ON position, after electrode harness has been secured in place but before the electrodes have been connected to terminals 62-64. In response to toggle switch 214 activated to the ON condition, the programmed computer in housing 17 activates display 31 to cause the characters E1 to be displayed on display 31. Printed table 213 below keyboard 212 provides the operator with an indication that E1 is maximum heart rate, in beats per minute. The operator then activates keys 201-210 with maximum heart rate for the subject, as determined from a table. After entry of the maximum heart rate, display 31 is activated to display the numerical values associated with the depressed keys 201-210. The operator then looks at display 31 to assure that the correct keys have been depressed. If he is satisfied that the correct keys have been depressed, enter key 211 is depressed. After depression of enter key 211, display 31 is activated by signals from the computer within housing 17, to display characters E2. The operator is then advised from printed table 213 that he is to enter minimum heart rate, in beats per minute, as determined from a table. The process is then repeated for resting heart rate, in beats per minute, determined upon awakening, and stride length, in inches, determined by measuring the stride of the subject, in accordance with entries E3 and E4, respectively, from printed table 213.

After stride length has been entered by activating key 211, display 31 is energized by the computer in housing 17 to display characters E5. In response to display of E5 on display 31, the operator presses key 201 or 210, depending upon whether the subject being tested is a male or female. Then, the computer activates display 31, to cause characters E6 to be displayed. Thereafter, the operator enters the age, fitness factor and weight, in pounds, for the subject in response to energization of display 31 for the characters E6, E7 and E8. Fitness factor can be determined from a table or a previous calculation by the computer.

If the operator realizes that he has made an entry error after enter key 211 is depressed, clear entry button 216 is depressed. In response to depression of key 216, the program in the computer within housing 17 goes back to a starting condition, wherein characters E1 are displayed on display 31. The operator then goes through the sequence E1-E8.

After all of the parameters (E1-E8) for the subject have been entered, the electrodes in harness 12 are connected to the computer by way of jacks 62-64. The operator then presses start key 60 on the top of housing 17, after which heart rate key 59 is depressed. The operator then monitors display 31 to observe the heart rate of the subject, to verify that the system is correctly connected. Housing 17 is then attached to waist band 16 or harness 12. When the subject is ready to begin the exercise routine, stop/store key 58 is depressed, followed by depression of start key 60. While the subject is performing the exercise routine, the parameters of interest can be monitored by pressing any one of keys 53, 54, 55, 57 or 59. The aural indicator is activated each time a heart beat occurs, when the heart beat rate reaches the minimum value set in response to characters E2. If the maximum heart rate, set in response to characters E1, is exceeded, the aural signal is constantly derived. If fitness coefficient is desired, the exercise routine is performed for 12 minutes, after which key 56 is depressed.

Typical configurations for a pedometer that can be mounted in instrument housing 17 are illustrated in FIGS. 6–8. In each of the pedometers, an output pulse is derived in response to each stride of the subject. Basically, each pedometer includes an inertial member which closes a circuit each time that the subject takes a stride to produce a pulse having a relatively short duty cycle. The frequency of the pulses is dependent upon the speed which the subject is traveling, as well as the length of the stride of the subject. Each of the pedometers is basically an accelerometer with an adjustable trigger point that is responsive to changes in acceleration equivalent to the foot of the subject hitting the ground, in response to the subject having covered the distance of one stride length.

In the pedometer of FIG. 6, a horizontal pendulum, including cantilevered arm 71, having weight 72 attached to the free end thereof, is mounted to pivot on stud 73. The end of arm 71 adjacent stud 73 is connected to one end of compression spring 74, the other end of which is fixed. Arm 71, weight 72 and stud 73 are metal to provide an electrically conducting path between a lead wire connected to stud 73 and a lead wire connected to a metal horizontally extending electric contact layer 75 that is engaged by weight 72 once each stride of the subject. Below metal layer 75 is a dielectric shock absorbing rubber layer 76, having an exposed, upper face extending parallel to the surface of layer 75. The compression of spring 74 is adjustable to control the trigger point between weight 72 and layer 75. Connected between the lead wires for stud 73 and layer 75 are input terminals of pulse generator 77 which derives a relatively short duration pulse each time weight 72 contacts layer 75. Thereby, the number of pulses derived from generator 77 is indicative of the number of strides taken by the subject. Pulses from generator 77 are supplied to the computer means within instrument housing 17.

In a second configuration for the pedometer, a conventional microswitch including housing 81, attached to cantilevered lever 82, is secured in place in housing 17 so that the lever extends generally in the horizontal direction. At the free end of lever 82 is fixedly secured a weight that is tuned to the inertial characteristics of lever 82. Thereby, in response to each stride of the subject, lever 82 is deflected downwardly, causing contacts within microswitch 81 to be closed. Input terminals of pulse generator 84 are connected across contacts of microswitch 81, so that the pulse generator derives an output pulse each time the contacts of the microswitch are closed.

In the configuration of FIG. 8, the pedometer includes a plastic sleeve 86 having a threaded internal bore into which metal screw 87 is threaded. The other end of sleeve 86 is closed by dielectric shock absorber 88. The face of shock absorber 88 inside of sleeve 86 is fixedly secured to metal compression spring 89 to which is connected an electric lead wire 91 that extends through a small aperture in the end of sleeve 86 proximate shock absorber 88. Fixedly secured to the end of spring 89 remote from shock absorber 88 is a metal ball 92. In a rest condition, spring 89 is compressed so that an open electric circuit exists between lead wire 91 and screw 87. In response to each stride of the subject, however, the inertia of sphere 92 causes compression spring 89 to expand, to complete a circuit between lead 91 and screw 87. Completion of the circuit between screw 87 and lead 91 is sensed by pulse generator 92, having input terminals electrically connected to lead wire 91 and screw 87.

Figure 9:
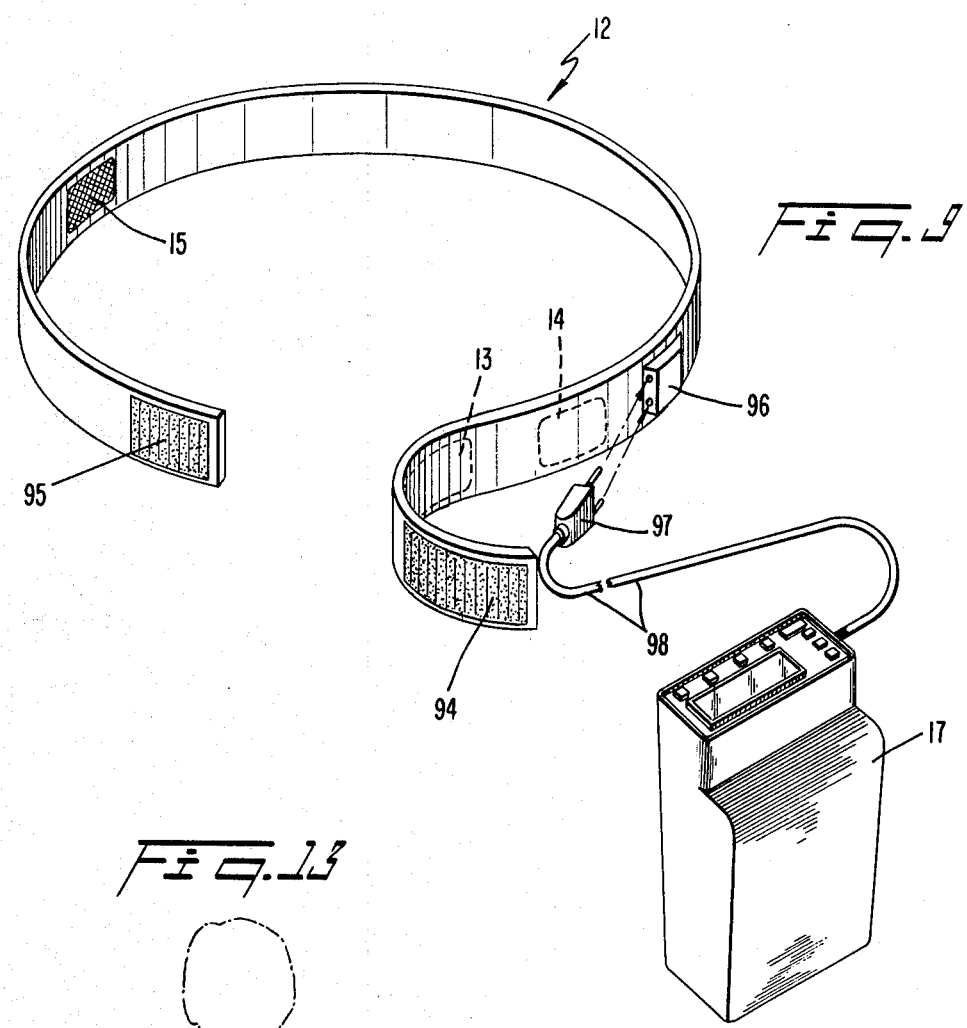
FIG. 9 is a perspective view of an electrode carrying chest strap in combination with a cable and the instrument housing.

An arrangement for connecting electrodes 13–15 of chest strap 12 to instrument housing 17 is illustrated in FIG. 9. Chest strap 12 is fabricated of a flexible cloth material having Velcro fastener pads 94 and 95 at opposite ends thereof. Electrodes 13–15 are sewn into chest strap 12 so that gel layers 21 thereof are exposed on the interior surface of the chest strap. Lead wires 24 from electrodes 13–15 extend interiorly through chest strap 12 to male connector 96, mounted on the outside of the chest strap. Connector 96 includes three female pins which are surrounded by a metal shield. The three female pins and shield of connector 96 are selectively engaged by a male connector 97, at one end of cable 98, the other end of which includes a male plug which is received by a female connector on a side of housing 17.

The voltages picked up or transduced by electrodes 13–15 have a tendency to have a common drift relative to a reference, i.e., ground, potential of the circuitry included within instrument housing 17. Circuitry is provided in instrument housing 17 to eliminate this drift, i.e., to provide common mode rejection. In addition, the circuitry filters out noise in electrocardiograph signals transduced by electrodes 13–15 and detects r pulses in the PQRST complex of pulses which is derived each time a heart beat of the subject occurs. The processing circuitry in housing 17 for the signals picked up by electrodes 13–15 also eliminates noise on the signal which is manifested by the occurrence of high amplitude pulses having a frequency greater than the possible heart beat rate of the subject.

Figure 10:
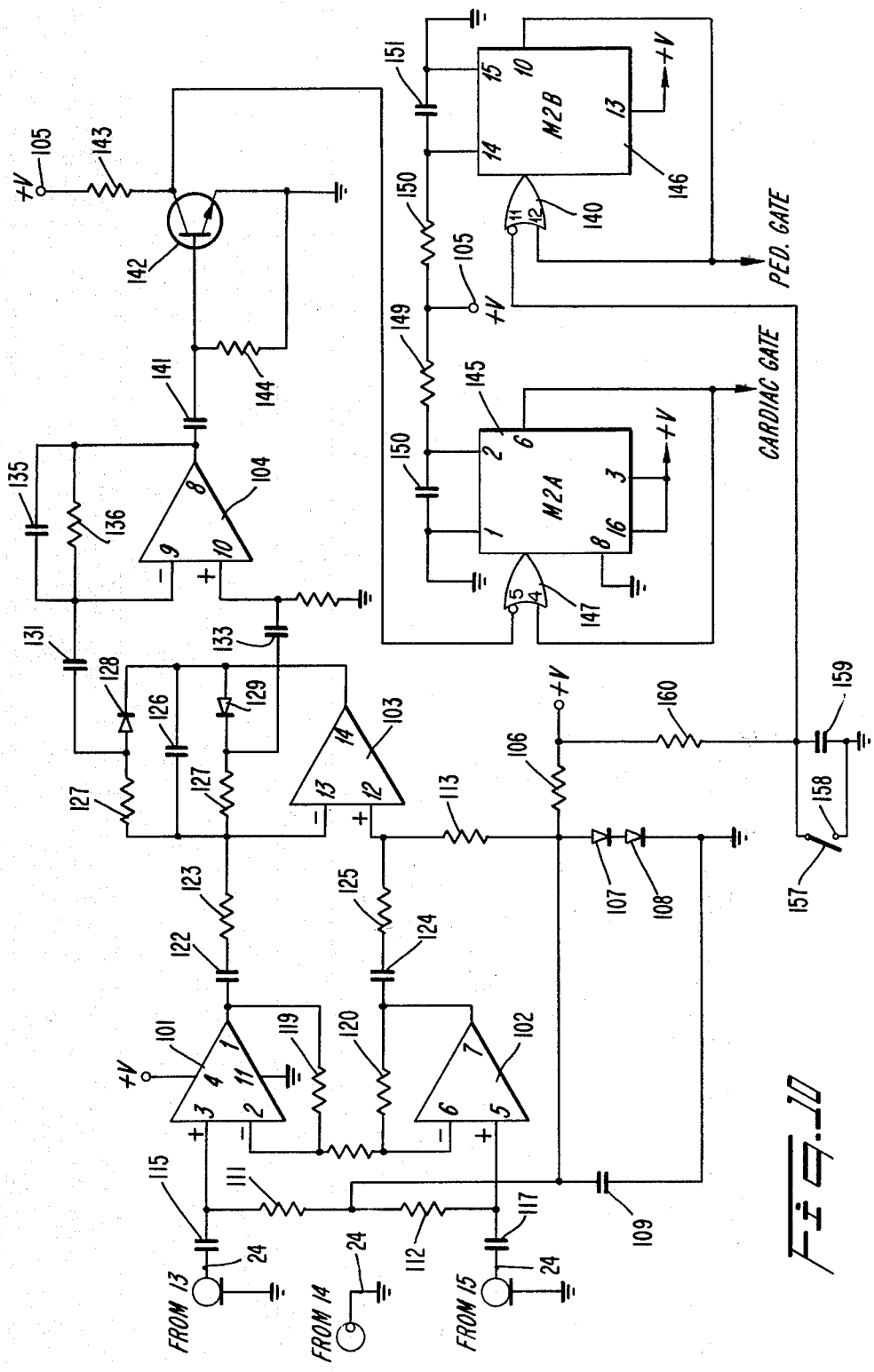
FIG. 10 is a circuit diagram of the electrocardiogram amplifier and filter circuitry in the instrument housing of FIG. 4.

To these ends, the processing circuitry in housing 17 for the voltages transduced by electrodes 13–15 is preferably of the type illustrated in FIG. 10. The circuitry illustrated in FIG. 10 is hybrid circuitry, including four differential, operational amplifiers 101–104 mounted on a common integrated circuit chip and having a common positive DC power supply terminal. Amplifiers 101–104 respond to the EKG signals transduced by the electrodes 13–15 and are connected to discrete components which enable a pulse to be derived each time an R pulse occurs in a QPRS complex of the subject.

To these ends, lead wire 24 of electrode 14 is connected to ground potential within instrument housing 17. The common or individual shields associated with lead wires 24 of electrodes 13–15 are also connected to ground in instrument housing 17.

The voltages on lead wires 24 from electrodes 13 and 15 are differentially combined in amplifiers 101, 102 and 103. In particular, the voltages on lead wires 24 from electrodes 13 and 15 are supplied to non-inverting input terminals of operational amplifiers 101 and 102, which non-inverting input terminals are also connected to a plus DC power supply voltage at terminal 105. The voltage at terminal 105 is derived from a battery, typically a 4.5 volt source, inserted through a suitable opening (not shown) in housing 17. The voltage at terminal 105 is reduced and regulated by a circuit including resistor 106, which is shunted by series diodes 107 and 108 and capacitor 109. The DC voltage developed across capacitor 109 is coupled to the non-inverting input terminals of amplifiers 101-104, so that these amplifiers can respond to both positive and negative DC voltages, even though a single, positive DC power supply is provided. The non-inverting input terminals of all of amplifiers 101-104 are referenced to a common potential across capacitor 109, by virtue of the connection of resistors 111-113 to the non-inverting input terminals of the amplifiers and a common terminal for resistor 106 and capacitor 109.

Amplifiers 101 and 102 are respectively coupled to the voltages derived from electrodes 13 and 15 by first and second series circuits respectively including capacitors 115 and 117. The gains of amplifiers 101 and 102 are stabilized by feedback resistors 119 and 120, respectively connected between the output terminals of amplifiers 101 and 102 and inverting input terminals of the amplifiers.

The output voltages of amplifiers 101 and 102 are respectively AC coupled to negative and positive input terminals of amplifier 103. The output of amplifier 101 is coupled to the inverting input terminal of amplifier 103 by a series circuit including capacitor 122 and resistor 123, while the output of amplifier 102 is coupled to the non-inverting input terminal of amplifier 103 by a series circuit including capacitor 124 and resistor 125.

To provide a low pass filter effect and full wave rectification for the voltages supplied to the inverting and non-inverting input terminals of amplifier 103, the amplifier includes a feedback circuit containing three parallel branches, each of which is connected between the output and inverting input terminals of the amplifier. In one of the branches is connected smoothing capacitor 126, while each of the other two branches includes a current limiting resistor 127, each of which is connected in series with oppositely polarized diodes 128 and 129.

Negative and positive voltages are respectively developed at the anodes and cathodes of diodes 128 and 129 and respectively coupled to the inverting and non-inverting input terminals of amplifier 104 by way of two separate high pass series resistance-capacitance circuits. In particular, the anode of diode 128 is connected to the inverting input terminal of amplifier 104 by a series capacitor 131 while the voltage at the cathode of diode 129 is coupled to the non-inverting input terminal of amplifier 104 by series capacitor 133. A feedback circuit, including the parallel combination of capacitor 135 and resistor 136, between the output terminal of amplifier 104 and the inverting input terminal of the amplifier provides low pass filtering for the differential signal derived at the output of amplifier 104.

Because of the full wave rectifying effect of diodes 128 and 129 and the differential connections between the outputs of amplifiers 101 and 102 to the input terminals of amplifier 103 and the dual outputs of amplifier 103 at diodes 128 and 129, the output of amplifier 104 is always a positive voltage, regardless of the manner in which the leads from electrodes 13-15 are connected to the circuitry within instrument housing 17. The circuitry described is a precision full wave, rectifying amplifier so the output voltage of amplifier 104 is a positive voltage that is a relatively accurate replica of each R pulse in a PQRST complex, regardless of whether electrode 13 or 15 is coupled to the inverting input terminal of amplifier 101, or regardless of whether the voltage from electrode 15 or 13 is coupled to inverting input terminal of amplifier 102.

Resistors 111, 112, 123 and 125, as well as capacitors 115, 117, 122, 124, 131 and 134, form a high pass filter having a low pass cutoff frequency of approximately 16 Hertz and a roll-off of 18 db per octave. Capacitor 126, resistors 127, capacitor 135, and resistor 136 form a low pass filter having a cutoff frequency of approximately 34 Hertz, with a roll-off of 12 db per octave. The resulting band pass filter derives a wave that is an accurate replica of the R wave of the PQRST complex with common mode rejection, so that the R pulse is stablized to a DC reference and noise which might be picked up by the electrodes is minimized.

The R pulse in a PQRS complex, being the highest amplitude pulse in the complex, is supplied to a clamping circuit including series capacitor 141 and normally back biased npn transistor 142, having a collector electrode connected to the DC power supply voltage at terminal 105 by resistor 143. The emitter collector path of transistor 142 is normally back biased to cutoff by resistor 144 that directly shunts the transistor emitter base junction, which functions as a shunt diode. In response to the R pulse being derived from the output of amplifier 104, the emitter base junction of transistor 142 is forward biased, whereby current momentarily flows through collector resistor 143, to lower the voltage at the collector of transistor 142 virtually to ground and the base-emitter junction of transistor 142 functions as a diode. The diode action of the emitter base junction of transistor 142 causes the base circuit to function as a positive peak detector for the R pulse, whereby the base can rise only about 600 millivolts above ground, but it can be driven considerably below ground by the output of amplifier 104. The negative voltage at the base of transistor 142 decays relatively slowly toward ground because of a 100 millisecond time constant of capacitor 141 and resistor 144, thereby virtually assuring a one-to-one relation between heart beats of the subject and the negative going pulses derived at the collector of transistor 142.

It is possible that noise may cause forward biasing of the base emitter path of transistor 142. Such noise is likely to occur at a frequency higher than the possible maximum heart beat rate of a person being tested; typically the maximum heart beat rate is approximately 240 beats per minute or 4 beats per second. To prevent such noise from being erroneously indicated as a heart beat, a timing circuit including one shot multivibrator 145 is provided.

In one preferred configuration, one shot 145 is part of an MC14538 dual one shot integrated circuit chip that also includes one shot 146 which functions as a pulse former for closing of pedometer switch contacts 157 and 158. One shots 145 and 146 include trigger inputs respectively responsive to the outputs of OR gates 147 and 148. OR gate 147 includes an inverting input terminal 5 responsive to the voltage at the collector of transistor 142 and non-inverting input terminal 4 responsive to the output of one shot 145, at terminal 6 of the integrated circuit. Input terminals 1 and 2 of the chip, for one shot 145, are connected to a timing circuit including series resistor 149 and capacitor 150, connected between the positive DC power supply voltage at terminal 105 and ground.

In response to a pair of adjacent pulses causing the base emitter path of transistor 142 to be forward biased successively in an interval greater than a predetermined interval equal to the minimum possible period between adjacent heart beats, e.g. 270 beats per minute, a pulse is derived from output terminal 6 of the dual one shot integrated circuit. The pulse derived from terminal 6 is applied across the electrodes of LCD indicator 51, to signal the subject each time he has a heart beat. In addition, the signal at terminal 6 is supplied to the digital computer means within housing 17. The signal at terminal 6 can be supplied to a telephone line by a suitable jack (not shown) on housing 17, for telemetering purposes. Because of the inability of a telephone line to handle very low frequency pulses, the pulses at terminal 10 are converted into a DC voltage, having an amplitude proportional to the pulse rate, with such a conversion being accomplished by averaging network (not shown), that is external to housing 17. The output of the averaging network is applied as a control input to a variable frequency oscillator (external to housing 17), which can be connected to a suitable communication link, such as a telephone line. However, if the output signal of transistor 142 is noisy, whereby pulses are derived from the collector of transistor 142 more often than the minimum period between adjacent heart beats, as determined by the values of resistor 149 and capacitor 150, OR gate 147 blocks passage of such a noisy signal from the transistor output to the trigger input of one-shot 145.

Each closure of pedometer switch contact 157 onto stationary contact 158, each time the subject takes a stride, causes the voltage across shunt capacitor 159 to be reduced substantially to ground, to produce a negative going pulse across capacitor 159, connected to the positive DC voltage at terminal 105 through resistor 160. The negative going pulses developed across capacitor 159 in response to each closure of contacts 157 and 158 are coupled through inverting input terminal 11 of OR gate 148 to a trigger input of one shot 146. Each such pulse is converted by one shot 146 into a pulse having a predetermined amplitude and duration. To this end, one shot 146 is connected to a timing circuit including resistor 150 which is connected in series with capacitor 151. Resistor 150 and capacitor 151 are connected in shunt between the DC power supply voltage from terminal 105 to ground, with capacitor 151 being connected between terminals 14 and 15 of one shot 146. Output terminal 10 of one shot 146 is coupled back to the trigger input of the one shot by way of a non-inverting input of OR gate 148. The connection between output terminal 10 of one shot 146 and non-inverting input terminal 12 of OR gate 148 causes the one shot to be wired in a non-retriggerable mode. The component values associated with one shot 146 and the connections to the terminals of the one shot and OR gate 148 are such that a maximum stride rate of 4 strides per second is achieved.

An alternate arrangement for detecting heart beats involves utilizing the well known phenomenon of photoplethysmography. Photoplethysmography relies on slight increases in infra red light absorption by capillaries on the skin of the subject. Typically, the capillaries are monitored in the fingertip, or some other suitable skin area, such as the brachialis muscle near the cephalic vein. The capillaries in these skin areas are close to the surface and expand slightly upon arrival of a systolic pressure wave, as occurs once for each heart beat. A sensor for the photoplethysmography phenomenon contains a light emitting diode and a photodiode; the sensor arrangement is placed over a selected skin area to monitor the infra red absorption change in the capillaries. Current supplied to the light emitting diode causes the skin area to be illuminated with light in the infra red spectrum, preferably at 0.9 microns wave length. Light derived from the light emitting diode is modulated by a relatively small (1-2%) heart pulse absorption signal. The resulting change in reflected light is sensed by a photodiode. One prior art apparatus for monitoring heart rates utilizing the photoplethysmography phenomenon, commercially available from Hughes Solid State Product, is packaged as an integrated circuit HLSS-05533D.

Figure 12:
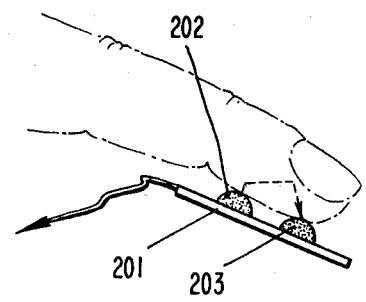

Referring more particularly to FIG. 12, the photoplethysmography phenomenon is detected by circuitry on a rigid board 201 which is attached to the fingertip by a suitable ring (not shown). On board 201 are mounted infra red light emitting diode 202 and infra red photodiode 203. Light emitting diode 202 and photodiode 203 are mounted on board 201 in such a position that infra red energy emitted from the light emitting diode is reflected by a vein in the fingertip to the photodiode. In response to the systolic pressure wave which occurs in the fingertip vein in response to each heart beat, the absorption characteristics of the vein change. The absorption change is detected by circuitry responsive to an output signal of photodiode 203. Leads in a cable (not shown) are connected from housing 17 to light emitting diode 202 and photodiode 203, to power the light emitting diode and to couple the analog signal derived from the photodiode back to processing circuitry within housing 17. The processing circuitry is merely a pulse generator, similar to the pulse generator responsive to pedometer switches 157 and 158, and replaces much of the circuitry associated with processing of the electrocardiogram signals derived from the electrodes in harness 12.

Figure 13:
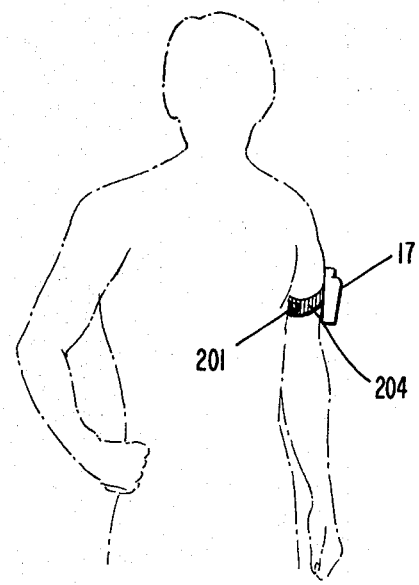
FIGS. 12 and 13 are illustrations of alternative devices for monitoring heart beats using photo-plethysmography.

In accordance with a modification of the apparatus illustrated in FIG. 13, board 201 is mounted on strap 204 so that light emitting diode 202 and photodiode 203 monitor systolic pressure pulses in the cephalic vein adjacent the brachialis muscle. Diodes 202 and 203 are connected via leads in strap 204 to housing 17, which is also mounted on strap 204. Housing 17 includes the pedometer, calculator and display devices, as described supra.

Figure 11A:
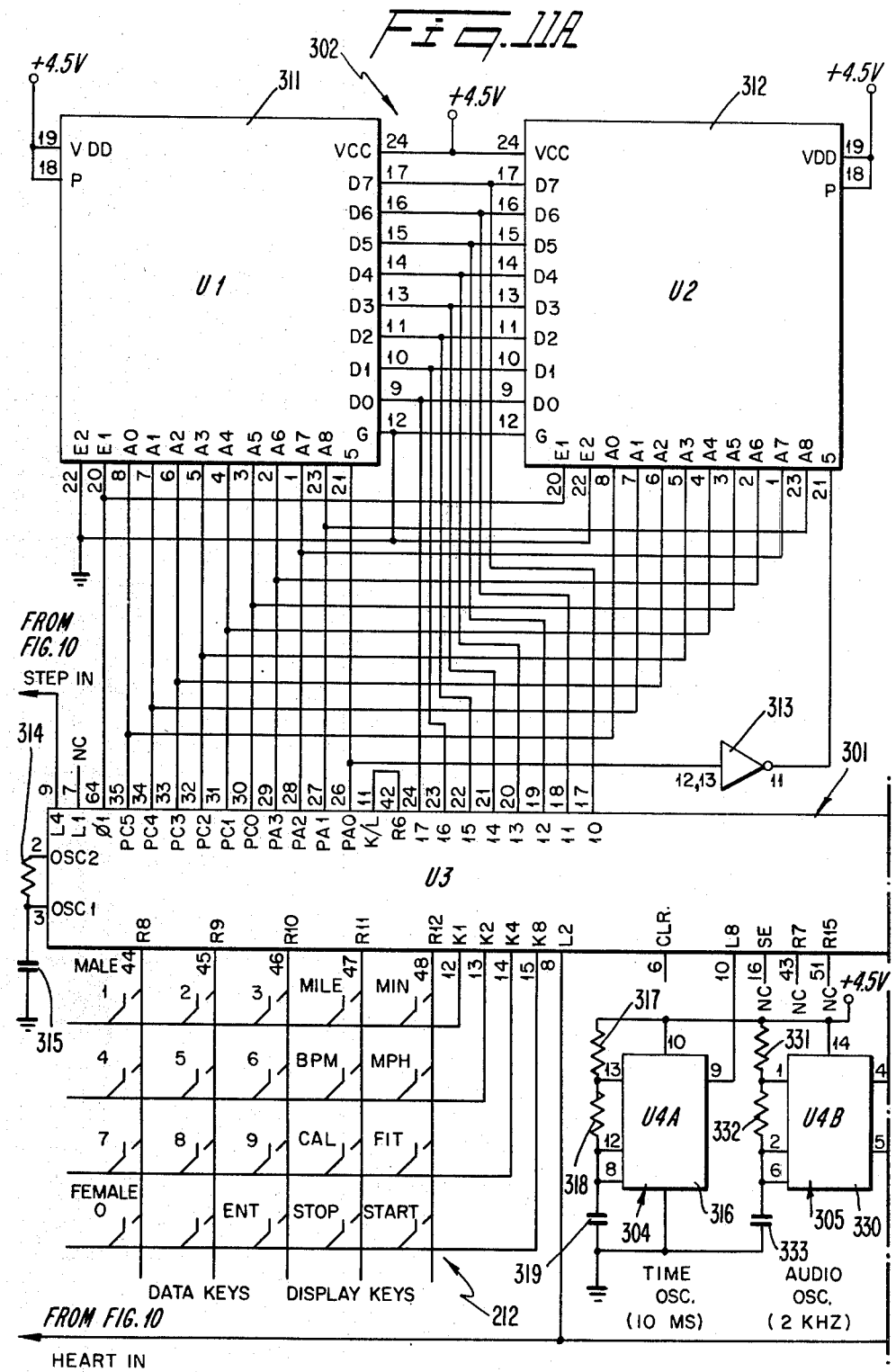
FIGS. 11a and 11b, together form a block diagram of the apparatus contained in the instrument housing, as well as of the electrodes.
Figure 11B:
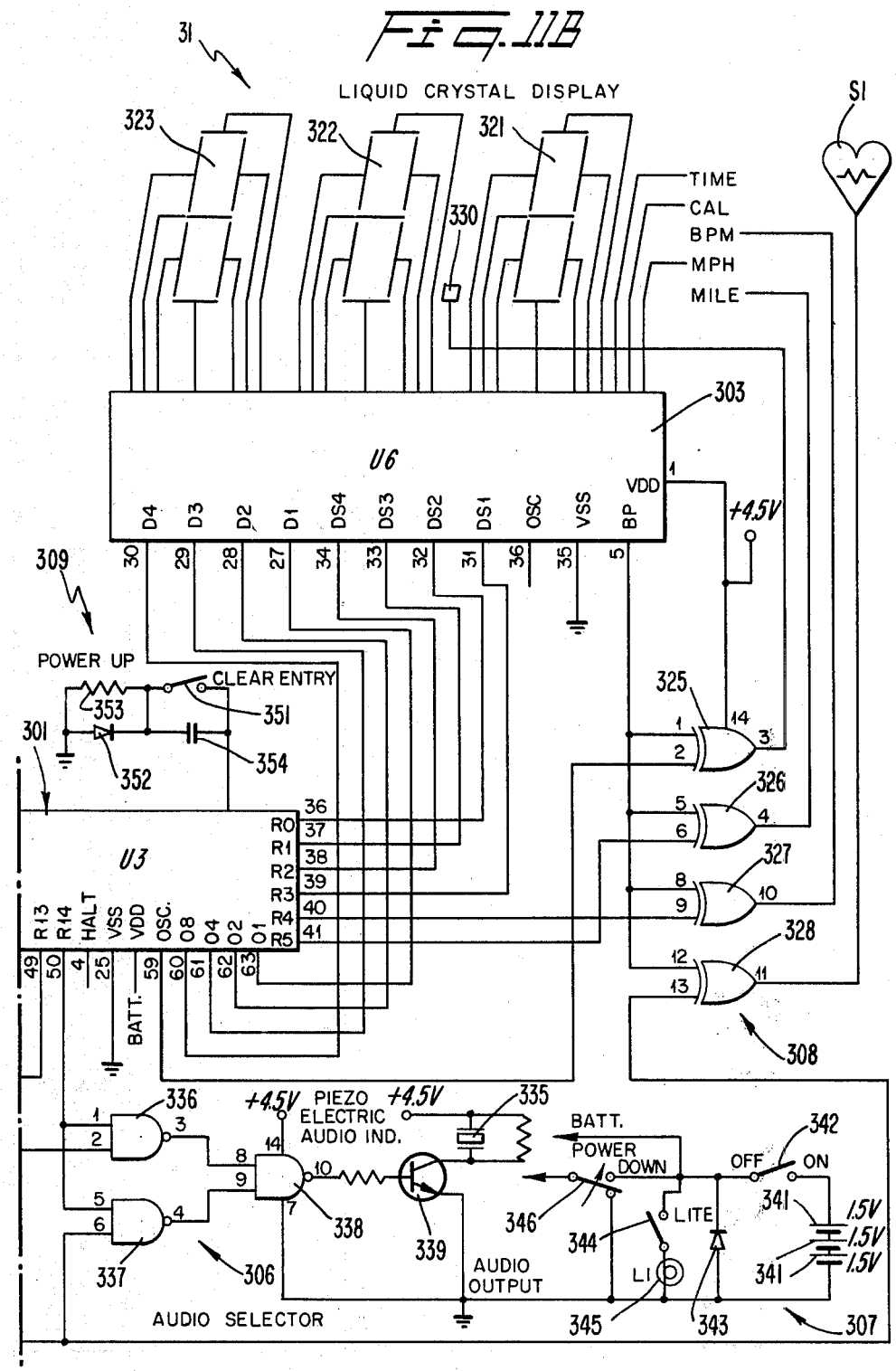

Reference is now made to the system block diagram, FIG. 11, to provide an indication of the overall organization of the electronic circuitry included in the present invention. All of the elements illustrated in the block diagram of FIG. 11 are located either on the surface or inside of housing 17. In addition, the circuitry of FIG. 10 is included in housing 17. The electronic circuitry illustrated in FIGS. 11a and 11b can be subdivided into a number of segments, namely: a 40 pin microcomputer 301, an erasable programmable read only memory 302, controller 303 for liquid crystal display 31, a ten millisecond oscillator 304, a 2-KHZ audio oscillator 305, audio selector and output circuitry 306, DC power supply 307, driver circuitry 308 for controller 303 and liquid crystal heart display 51, power up circuitry 309, as well as keyboard 212.

In a preferred configuration, microcomputer 301 is a 40 pin Texas Instrument TMS 1099JLC unit including an internal arithmetic logic unit, accumulator, random access memory and oscillator. The arithmetic logic unit in microcomputer 301 responds to signals from time oscillator 304, pedometer signals from one shot 146, FIG. 10, heart beat signals from one shot 145, FIG. 10, and keyboard 212. The arithmetic logic unit within microcomputer 301 responds to these signals, combines them and stores them in a 4-bit accumulator for processing. Outputs of the accumulator are supplied to output latches O1–O8 and O1L, as well as to the random access memory and arithmetic logic unit within microcomputer 301. Data are stored in the random access memory in microcomputer 301 as 64, 4-bit words. The 4-bit words are conveniently grouped into four 16-word files addressed by a 2-bit index register included in the microcomputer. A second 4-bit register within microcomputer 301 addresses one of the sixteen words in one of the four files within microcomputer 301.

The program which controls microcomputer 301 is stored in erasable programmable read only memory 302. Memory 302 includes two separate 1K memory elements 311 and 312, each of which in a preferred embodiment is a complementary metal oxide semiconductor memory, type IM66541JG, available from Texas Instruments. Memory elements 311 and 312 are addressed in response to signals supplied by microcomputer 301 to output terminals PA0–PA3 and PC0–PC5 thereof. The addressing signals are supplied to input terminals A0–A8 of memory elements 311 and 312, with a selection of one of the memory elements being in response to opposite valued signals supplied to terminals 5 of memory elements 311 and 312 from terminal PA0 of microcomputer 301. The output at terminal PA0 is applied directly to terminal 5 of memory element 311, and to terminal 5 of memory element 312 by way of inverter 313. Memory elements 311 and 312 include parallel data output terminals D0–D7 which are applied to input terminals I0–I7 of microcomputer 301. Microcomputer 301 responds to the signals at terminals I0–I7 to control the coupling of signals between the various inputs and outputs of the microcomputer and between the elements within the microcomputer. Microcomputer 301 operates with a basic instruction cycle of ten microseconds, to provide ten thousand instructions per second, due to the values of resistor 314, connected between microcomputer terminals OSC1 and OSC2, as well as capacitor 315, which shunts terminal OSC1 to ground; terminals OSC1 and OSC2 are connected to the oscillator in the microcomputer.

Heart beat and pedometer signals, respectively derived from one shots 145 and 146, FIG. 10, are supplied to input terminals L2 and L4 of microcomputer 301. Input terminals K1, K2, K4 and K8 of microcomputer 301 are responsive to closure of switches in keyboard 212 in response to depression of keys 201–210 and pushbuttons 53–60. Key switches in keyboard 212 are arranged in a four-row by five-column matrix, with the four rows of the matrix supplying signals to input terminals K1, K2, K4 and K8 of microcomputer 301. Column leads in keyboard 212 are sequentially responsive, on a time multiplex basis, to signals supplied by microcomputer 301 to output terminals R8, R9, R10, R11 and R12 thereof. Closure of the switch associated with start button 60 causes a pulse to be supplied to input terminal K8 of microcomputer 301 when the microcomputer is supplying a pulse to output terminal R12 thereof. The duration of the start switch closure is always sufficiently long compared to the normal operating cycle of microcomputer 301 to assure coupling of a pulse to input terminal K8, which pulse sets accumulators in microcomputer 301 to zero, and enables monitoring of other parameters by the microcomputer to be initiated. Closure of the switch associated with stop/store button 58 causes a pulse supplied by microcomputer 301 to terminal R11 to be coupled to terminal K8, to freeze the last calculated display values in memory, and enable them to be constantly supplied to liquid crystal display 31 by controller 303.

Time oscillator 304 supplies ten millisecond pulses to input terminal L8 of microcomputer 301 to enable the microcomputer to calculate elapsed exercise time, running speed, fitness factor and other related parameters. Oscillator 304 includes an integrated circuit chip, in a preferred embodiment an ICM 7556 IPD chip, available from Texas Instruments. The periodicity of pulses derived from an oscillator in chip 316 is determined by the values of a timing circuit including resistors 317 and 318, in combination with capacitor 319. The series combination of resistors 317 and 318, as well as capacitor 319, is connected between a positive DC supply voltage and ground, with a tap between resistor 317 and 318 connected to terminal 13 of chip 316, and a tap between resistor 318 and capacitor 319 connected in parallel to terminals 8 and 12 of chip 316. Chip 316 has an output terminal 9 connected to input terminal L8 of microcomputer 301. The signal supplied by oscillator 304 to microcomputer 301 is counted down by frequency dividers in the microcomputer into 0.01, 0.1, 1.0 and 10 second increments, as well as into 0.1, 1.0, 10 and 100 minute increments.

Microcomputer 301 is programmed in response to signals from memory 302 to respond to the signals applied to input terminals L2, K1, K2, K4, K8, L4 and L8 to calculate heart rate in beats per minute, distance traveled in miles, average speed of the distance traversed in miles per hour, energy consumption in kilocalories, and fitness factor, as well as to determine elapsed exercised time. These parameters are constantly being computed by microcomputer 301 and are selectively supplied to outputs thereof, in response to depression of keys within keyboard 212. Basically, microcomputer 301 multiplexes all of the inputs supplied to it to calculate these parameters, as well as to activate controller 303 with the various characters on program board 213. Microcomputer 301 is programmed in a conventional manner to perform these functions.

Beats per minute is determined by microcomputer 301 by combining the heart beat signal from one shot 145, as applied to terminal L2, with the output of time oscillator 304, as applied to terminal L8. Basically, microcomputer 301 responds to the signals applied to terminals L2 and L8 thereof to determine the length of time required for four beats of the heart. This time interval is divided by a constant, equal to 24,000. In other words, beats per minute is determined from:

$$\frac{24,000}{\sum_{B=0}^{4} T}$$

where, B equals number of heart beat signals, and T equals time in seconds.

Microcomputer 301 responds to the number of steps and time signals respectively applied to input terminals L4 and L8 thereof by one shot 146 and time oscillator 316, as well as a physiological signal for the subject, to calculate miles per hour. From the number of steps, as applied to terminal L4, and the initial entry of the stride length of the subject, as derived from keyboard 212 and stored in the random access memory of microcomputer 301, and a predetermined constant relating inches to miles, the microcomputer calculates total distance in tenths of miles. From the calculation of tenths of miles, miles per hour is calculated from:

(60D/T)

where D equals distance in miles, and T equals time in minutes.

The fitness factor of the subject is calculated by microcomputer 301 after the subject has exercised to his maximum capability for twelve minutes. To determine fitness factor, microcomputer 301 responds to signals supplied to input terminals L4 and L8 thereof from one shot multivibrator 146 and time oscillator 304, as well as activation of one of gender keys 201 or 210 and age key. In response to the signal from one shot multivibrator 146 and the previously inputted stride length signal and a predetermined constant relating stride length in inches to meters, distance traversed is determined by microcomputer 301. After twelve minutes of maximum capacity exercising, the fitness factor is computed in response to a pulse generated in microcomputer 301. Hence, the time of the exercise is not a factor entering into the calculation of fitness, but is employed to determine when the fitness factor calculated should be terminated. Absolute fitness factor is calculated in response to the signals supplied to microcomputer 301 as:

$$F = \left[ \frac{Dm - a}{12} - b \right] c + d$$

where
F = absolute fitness factor
Dm = distance traversed in meters for 12 minute exercise
b, c and d are predetermined constants determined from Dr. Cooper's book.

From the calculation of F, actual fitness factor for a male 15 years of age or older is calculated by microcomputer 301 as:

$$F_m = \frac{eF}{g - age} ;$$

for a female 15 years of age or older, actual fitness factor is calculated by microcomputer 301 as:

$$F_f = (F_m/h)$$

where e, g and h are predetermined constants determined from Dr. Cooper's book.

Calorie consumption is computed by microcomputer 301 from exercise heart rate, as coupled to input terminal L2 of the microcomputer from one shot 145, resting heart rate, as supplied to the microcomputer from keyboard 212, heart beats per MET, which is directly proportional to fitness factor, milliliters of oxygen per minute per pound, which is directly proportional to weight in pounds of the subject, as supplied to microcomputer 301 by keyboard 212, as well as a function of sex of the subject. Microcomputer 301 computes heart beats per MET as:

$$C = jF' + m$$

where F' = fitness factor computed for the male or female subject, i.e., $F_m$ or $F_f$;
j and m are predetermined constants.

Computer 301 calculates milliliters of consumed oxygen for male subjects as:

$$K_m = nW = P$$

and for female subjects as:

$$K_f = (K_m/q),$$

where W = weight of the subject and m, p and q are predetermined constants. Microprocessor 301 responds to these factors to compute calories per minute in accordance with:

$$\left( \frac{B - R}{C} \right) - vK$$

where
B = exercise heart rate in beats per minute;
R = resting heart rate in beats per minute;
K is given supra; and
v is a predetermined constant.

The equations and constants for the calculation of calories per minute are based on a so-called mixed diet of carbohydrates, fat and protein.

The calories per minute of exercise equations were evolved from a review of the literature and known research, in particular in the book "Physical Fitness and Weight Control", Sharkey, Mountain Press Printing Company, 1974. It is known that the calorie consumption of the human body is directly proportional to oxygen consumption. If oxygen consumption could be directly measured, calories consumed would be related to oxygen consumption as a direct proportionality function. However, direct measurements of oxygen consumption can only be attained using sophisticated and cumbersome equipment. Thus, if it is desired to determine the calorie consumption of a subject undergoing physical activity, such as running, an indirect measurement of oxygen consumption must be made.

The hypothesis for the calorie consumption equations employed in the present invention relies upon several known phenomena. The first phenomenon is that under normal conditions there is a roughly linear relationship between oxygen uptake and heart rate during exercise for a particular subject. The roughly linear relationship has a slope that changes with the physical fitness of the subject. This is because a physically fit person is able to transport the same amount of oxygen at a lower heart rate than an unfit person. The relationship between oxygen uptake and heart rate is generally independent of sex and age, although females require higher heart rates to transport the same amount of oxygen as males. The second phenomenon relies upon the concept of METs (multiples of the metabolic need for sitting quietly) to quantify workloads of subjects undergoing exercise. The METs concept assumes that energy requirements of a subject at rest are substantially constant for a given unit of body mass. The oxygen requirement for one kilogram of body weight depends on total body weight. On average, the oxygen requirement for one kilogram of body weight is 3.5 milliliters per minute at rest, i.e., at one MET. Depending upon the source of fuel utilized by the subject (fat and/or carbohydrates), the caloric equivalent for one liter of oxygen amounts to 4700 to 5000 calories. Thus, the caloric equivalent of one MET is, on the average, 70 calories per minute per kilogram of body weight. The hourly caloric equivalent of one MET is then 1000 calories per kilogram. Assuming an exercise routine requires 10 METs, the hourly energy requirement is 10 kilocalories per kilogram, or a total of 750 kilocalories for a person with a weight of 75 kilograms.

A third factor, which has been employed and which occurs because of the linear relation between heart beat rate to oxygen uptake, is that heart rate increases are related to physical condition of the subject. This can be shown from the fitness tables in the books by Dr. Cooper and Dr. Sharkey as follows: heart beat rate change of eight beats per MET indicates superior physical condition; heart beat rate change of nine beats per MET indicates excellent physical condition; heart beat rate change of ten beats per MET equals good physical condition; heart beat rate change of eleven beats per MET indicates fair physical condition; heart beat rate change of twelve beats per MET indicates poor physical condition; and heart beat rate change of thirteen beats per MET indicates very poor physical condition.

A fourth factor which has been relied upon is the relationship between oxygen and calorie consumption. It has been determined that each liter of oxygen consumed is the equivalent of 4.7–5.0 kilocalories of energy. The range of 4.7–5.0 kilocalories is further defined by considering that under normal conditions athletes depend upon carbohydrates and fats as muscular energy sources. If all of the energy from a physical activity comes exclusively from carbohydrates or from fat, a person respectively uses 5.05 or 4.60 kilocalories per liter of oxygen. Most subjects, however, rely upon energy from both sources during an exercise routine. At rest, and while sprinting, most, if not all, energy comes from carbohydrates. Long duration exercise, 2 hours or more, requires energy consumption to come from body fat. However, when a person exercises aerobically for 10 to 30 minutes, 60% of the energy comes from fat and 40% comes from carbohydrates. Therefore, 4.825 calories per minute per liter of oxygen is an appropriate factor to be employed in microcomputer 301.

Because basal metabolism rates drop about ½–1% a year for each year past the age of 26 for male, and for each year past the age of 21 for female, calorie consumption in the equation is adjusted downwardly at the rate of approximately ½% for each year above 26 for males and for each year above 21 for females. Thus, microcomputer 301 also responds to the age input from keyboard 212 to calculate calories per minute of exercise. Microcomputer 301 responds to the inputs to update calories per minute of exercise once a minute. Each of the updated calories per minute of exercise values is supplied to an accumulator and then is stored in the random access memory of the microcomputer, so that the subject is able to determine total calorie consumption.

Microcomputer 301 has four outputs R0–R3 and 01–08 which drive eight inputs of liquid crystal display controller 303. In a preferred embodiment, display controller 303 is an integrated circuit element, with a nomenclature ICM 7211 AIPL. Display controller 303 responds to the signals applied by microcomputer 301 to input terminals D1–D4 and DS1–DS4 to energize three liquid crystal display characters 321, 322 and 323 in liquid crystal display 31. Each of characters 321, 322 and 323 includes seven segments, arranged in a straight line so that when all segments of a character are activated, the character appears to be the numeral 8. Segments of characters 321, 322 and 323 are selectively activated in response to signals supplied to input terminals D1–D4 and DS1–DS4 of controller 303 to enable display of 16 characters, viz: 0, 1, 2, 3, 4, 5, 6, 7, 8, 9, H, E, L and P, as well as a blank. Controller 303 includes, internally thereof, a self-contained resistance capacitance oscillator, a divider chain, a backplane driver, and 28 segment outputs, for four different characters. The 28 segment outputs provide a zero DC component signal necessary for a long display life for the liquid crystals in display 31. Controller 303 is supplied with true binary signals from microcomputer terminals 01, 02, 04 and 08. The data from microcomputer 301 are strobed into controller 303 under the control of outputs R0–R3 of microcomputer 301. The least most significant digit output of controller 303 is strobed under the control of the signal at output terminal R2 of microcomputer 301, while the most significant digit of controller 303 is strobed under control of the signal at terminal R3. Only three of the available eight segments are used in the least significant bit position of the output of controller 303 to control annunciators associated with time button 57, calorie button 55 and miles per hour button 54.

Controller 303 includes a further output terminal BP which is energized in response to a predetermined state of the segment supplied by terminals 01, 02, 04 and 08 to controller 303 to enable the gates of gate array 308 simultaneously by virtue of a parallel input to the gates from terminal BP. Four exclusive OR gates 325–329 are included in gate array 308. Gate 325, responsive to a signal at output terminal OSL of microcomputer 301 includes an output terminal connected to drive decimal point 330 in liquid crystal display 31, which decimal point is positioned between characters 321 and 322. Gate 326, connected to output terminal R5 of microcomputer 301, when biased by the signal at terminal BP of controller 303, drives an annunciator associated with distance key 53. Gate 327 has an input terminal responsive to the signal at output terminal R4 of microcomputer 301 and an output terminal connected to drive an annunciator associated with beats per minute push button 59. Exclusive OR gate 328 has an input responsive to one shot 145 and an output which drives an annunciator associated with heart LCD 51. Thereby, heart LCD 51 is activated for each heart beat pulse derived from one shot 145. The annunciators responsive to the outputs of exclusive OR gates 325–328 for the time, calories, and miles per hour outputs of controller 303 are not shown but are conventional and obvious to those skilled in the art; for example, the annunciator associated with the time, calorie, beats per minute, miles per hour and mile outputs of controller 303 and gates 325–328 are connected in series with the switches in keyboard 212 with which they are associated.

The aural indications derived from the speaker behind screen 52 are selectively derived. The aural signal has a tone at a fixed frequency of 2 kilo Hertz, as derived from audio oscillator 305. Audio oscillator 305 is preferably an integrated circuit chip, type ICM 7556 IPD, having a frequency determined by the values of resistors 331 and 332, connected in series with each other and capacitor 333. The series circuit including resistors 331 and 332, as well as capacitor 333, is connected between a plus DC power supply voltage and ground. A tap between resistors 331 and 332 is connected to input terminal 1 of chip 330; a tap between resistor 332 and capacitor 333 is connected in parallel to input terminals 2 and 6 of chip 330. Chip 330 is selectively activated in response to an output signal of microcomputer 301 at terminal R13.

The audio output signal of oscillator chip 330, at terminal 5 thereof, is selectively gated to piezo electric audio indicator 335 which drives the speaker behind grill 52 in response to the heart beat output signal of one shot 145 and the output signal at terminal R14 of microcomputer 301. The signals are combined in an array of NAND gates including NAND gates 336, 337 and 338, each of which includes two input terminals. The two input terminals of NAND gate 336 are respectively responsive to the output signal of oscillator chip 330, at terminal 5 thereof, and the output of microcomputer 301 at terminal R14, which also drives one of the inputs of NAND gate 337. The remaining input of NAND gate 337 is responsive to the heart beat output signal of one shot 145. Output signals of NAND gates 336 and 337 are combined in NAND gate 338, having an output which is DC coupled to the base of NPN transistor 339, connected in the common emitter mode, so that piezo electric crystal 335 is connected between a positive DC power supply voltage and the transistor collector. Gates 336–338 are connected to be responsive to the output signals of one shot 145, integrated circuit chip 330 and the signal at terminal R14 of microcomputer 301, and terminal 4 of chip 330 is responsive to the signal at terminal R13 of microcomputer 301, so that: (1) no audio signal is derived from piezo electric crystal 335 in response to binary zeros being derived at output terminals R13 and R14 of microcomputer 301; (2) an audio output signal is derived from crystal 335 in response to each heart beat pulse derived from one shot 145, when binary one and zero signals are respectively derived from terminals R13 and R14 of microcomputer 301; and (3) a continuous two KHz audio output signal is derived from crystal 335 in response to binary one signals being derived from output terminals R13 and R14 of microcomputer 301.

DC power is supplied to the circuit components illustrated in FIGS. 11a and 11b by a power supply network including three series AA dry cells 341, each of which has a voltage of 1.5 volts. Dry cells 341 are selectively connected to the circuitry through switch contacts 342 which are responsive to movement of toggle switch 214, FIG. 5a. The voltage supplied through switch contacts 342 is regulated by back biased diode 343, across which is connected the parallel combination of light switch 344 and light emitting diode 345, which corresponds with lamp 61, on housing 17. For the power down situation, the voltage developed across diode 343 is selectively applied by switch contact 346, when the device is not in the power down state, to all of the active circuit elements of FIGS. 10, 11a and 11b, except microcomputer 301. Of course, memory elements 311 and 312 remain programmed even though they are not supplied with power by way of switch 346 because they are read only memories. Power is continuously applied to microcomputer 301, regardless of the position of switch 346, as long as switch 342 is closed, by virtue of the connection of switch contact 342 to terminal BATT of microcomputer 301. Thereby, the random access memory within microcomputer 301 stores data during the power down mode, to minimize the drain on batteries 341; with switch 346 opened and switch 342 closed, so power is applied only to microcomputer 301, the drain from dry cells 341 is approximately 1 microampere.

Power up circuit 309 sets the random access memory of computer 301 to a predetermined programmed position for initiation and execution of the program algorithm stored in the read only memory 302. Power up circuit 309 also includes switch 351, which is responsive to depression of clear entry button 216. Power up circuit 309 includes back biased diode 352, shunted by resistor 353. The parallel combination of diode 352 and resistor 353 is connected by capacitor 354 to terminal 5 of microcomputer 301. Capacitor 354 is selectively short circuited by closure of switch contacts 351, which also sets microcomputer 301 to the predetermined initial program position for execution of the program algorithm stored in read only memory 302.

While there have been described and illustrated several specific embodiments of the invention, it will be clear that variations in the details of the embodiments specifically illustrated and described may be made without departing from the true spirit and scope of the invention as defined in the appended claims. For example, the invention can be used by physicians in conjunction with a conventional EKG chart recorder responsive to the EKG signal derived from amplifier 103, FIG. 10. Also, other parameters of interest can be computed, e.g., heart recovery time can be determined by responding to the heart rate pulses and the clock pulses to determine when heart rate reaches a predetermined relatively low level, such as the minimum heart rate.

We claim:

1. Apparatus for testing the physical condition of a subject comprising means adapted to be mounted on the subject for monitoring and deriving a first signal indicative of heart activity of the subject, means adapted to be mounted on the subject for deriving a second signal indicative of distance traversed by a limb of the subject during testing, input means for deriving at least one signal indicative of a predetermined physiologically relevent parameter of the subject, said parameter having a constant, predetermined value, a clock source for deriving a timing signal during testing of the subject, and computer means responsive to the first, second, predetermined physiologically relevant parameter and timing signals for calculating the magnitude of a signal indicative of physical activity of the subject being tested in response to the values of said first and second signals, said physiologically relevant parameter signal and said timing signal, and indicator means responsive to the physical activity signal.

2. The apparatus of claim 1 wherein the first signal deriving means includes means for monitoring the number of heart beats of the subject.

3. The apparatus of claim 2 wherein the means for monitoring the number of heart beats includes electrodes adapted to be on the subject for deriving an electrocardiogram signal.

4. The apparatus of claim 3 wherein the means for monitoring further includes means for detecting r pulses of the electrocardiogram signal to the exclusion of other pulses of the electrocardiogram signal.

5. The apparatus of claim 4 wherein the means for detecting r pulses includes a band pass filter for passing the r pulses and a clamping circuit for peaks of the r pulses.

6. The apparatus of claim 4 or 5 further including full wave rectifier means for the r pulses so that r pulses of only one polarity are applied to the clamping means regardless of the connections of the electrodes to the r pulse detecting means.

7. The apparatus of claim 4 or 5 further including means for preventing derivation of the first signal in response to a pair of adjacent detected r pulses occurring in less than a predetermined interval which is less than the possible period between adjacent beats of a heart.

8. The apparatus of claim 3 or 4 or 5 wherein three electrodes are provided on the subject, each electrode being associated with a lead wire, shield means for the lead wires, said three lead wires and shield means being connected to three sets of input terminals of an electronic instrument housing, each set of input terminals including a grounded terminal connected to the shield means and a signal input terminal, one of said signal input terminals being connected to a DC reference level, differential amplifier means responsive to voltages at the other two signal input terminals, and means for referencing the differential amplifier means to the reference level to provide common mode rejection for voltages generated by said electrodes.

9. The apparatus of claim 3 further including a garment for carrying and pressing the electrodes against the skin of the subject.

10. The apparatus of claim 9 wherein each of the electrodes includes a highly electrically conductive gel which adheres to the skin of the subject while moistened.

11. The apparatus of claim 10 wherein the gel includes karaya gum and glycerin.

12. The apparatus of claim 3 or 9 or 10 or wherein a first of the electrodes is adapted to abut on skin against the rib cage, in the vicinity of the heart of the subject, a second of the electrodes is adapted to abut on skin against the sternum of the subject, and a third electrode is adapted to abut on skin just below the right chest quadrant of the subject.

13. The apparatus of claim 3 further including a chest strap for carrying and pressing the electrodes against the skin of the subject, wherein a first of the electrodes is carried by the strap so it is adapted to abut on skin against the rib cage, in the vicinity of the heart of the subject, a second of the electrodes is carried by the strap so it is adapted to abut on skin against the sternum of the subject, and a third electrode is carried by the strap so it is adapted to abut on skin just below the right chest quadrant of the subject.

14. The apparatus of claim 3 further including a brassiere for carrying and pressing the electrodes against the skin of the subject, wherein a first of the electrodes is carried by the brassiere so it is adapted to abut on skin against the rib cage, in the vicinity of the heart of the subject, a second of the electrodes is carried by the brassiere so it is adapted to abut on skin against the sternum of the subject, and a third electrode is carried by the brassiere so it is adapted to abut on skin just below the right chest quadrant of the subject.

15. The apparatus of claim 13 or 14 wherein each of the electrodes includes a highly electrically conductive gel which adheres to the skin of the subject while moistened.

16. The apparatus of claim 2 or 3 or 4 wherein the second signal deriving means comprises transducer means adapted to be carried by the subject for monitoring the quantity of repetitive actions taken by a limb of the subject.

17. The apparatus of claim 2 further including means for selectively applying the first signal to the indicator means.

18. The apparatus of claim 17 wherein the indicator means is aural, and means for pulsing the aural indicator in response to each heart beat, said pulsing means being activated when the computer means is responsive to at least a predetermined number of beats in a predetermined interval, as indicated by the first and timing signals.

19. The apparatus of claim 17 or 18 wherein the indicator means is aural, and means for continuously activating the aural indicator in response to the heart beat rate exceeding a predetermined level, said continuously activating means being activated when the computer means is responsive to the number of heart beats exceeding a certain number in a predetermined interval, as indicated by the first and timing signals.

20. The apparatus of claim 1 wherein the second signal deriving means comprises transducer means adapted to be mounted on the subject for monitoring the quantity of repetitive actions taken by a limb of the subject.

21. The apparatus of claim 20 wherein the transducer means comprises inertia means for deriving a pulse each time the limb completes a cycle of the repetitive action.

22. The apparatus of claim 21 wherein the transducer means comprises a pedometer, and the input means includes means for deriving a signal indicative of stride length, said computer means being responsive to pulses derived from the inertia means and the stride length indicating signal for deriving the second signal.

23. The apparatus of claim 22 wherein the indicator means is visual and further including means for selectively supplying the second signal to the visual indicator means.

24. The apparatus of claim 1 or 23 wherein the indicator means is visual and the computer means is responsive to the second signal and the timing signal for deriving a signal indicative of speed, and means for selectively supplying the speed indicating signals to the visual indicator means.

25. The apparatus of claim 1 or 23 wherein the first signal deriving means includes means for monitoring the number of heart beats of the subject and wherein the computer means is responsive to the first and timing signals for deriving a signal indicative of beats per unit length of time, said indicator being visual, and means for selectively supplying the signal indicative of beats per unit length of time to said visual indicator means.

26. The apparatus of claim 1 wherein the computer means includes a memory, means for supplying signals indicative of predetermined physiological parameters to the memory, a pair of terminals for a DC power supply for the computer means, signal deriving means, and indicator means, switch means for enabling the memory to store the signals indicative of the parameters while the remainder of the computer means, the signal deriving means and indicator means are decoupled from the DC power supply and for enabling new signals indicative of the parameters to be supplied to the memory.

27. The apparatus of claim 2 wherein the means for monitoring the number of heart beats includes means for detecting absorption changes of optical energy in a vessel of the subject in response to pressure waves resulting from beats of the heart.

28. The apparatus of claim 27 wherein the detecting means includes an infra red optical energy source and an infra red detector responsive to optical energy from the infra red source reflected from the vein.

29. The apparatus of claim 28 wherein the infra red source and infra red detector are mounted on a support adapted to be mounted on a fingertip of the subject.

30. The apparatus of claim 29 wherein the infra red source and infra red detector are mounted on a support adapted to be mounted on a brachialis muscle of the subject.

31. Apparatus for testing the physical condition of a subject comprising means adapted to be mounted on the subject for monitoring and deriving a first signal indicative of heart activity of the subject, an electronic instrument housing adapted to be carried by the subject, means for coupling said first signal to terminals on the instrument housing, said housing including: (a) an inertial member for monitoring the quantity of repetitive actions taken by a limb of the subject and for deriving a second signal indicative of said quantity, (b) a keyboard for enabling signals to be derived indicative of numerical quantities associated with a plurality of physiologically relevant parameters of the subject, (c) a clock source of deriving timing signals, (d) digital computer means responsive to the first, second, timing and keyboard signals for deriving plural digital output signals indicative of different physical activities of the tested subject, (e) visual digital indicator means, (f) plural key switches, each associated with a different one of the physical activities, and (g) means responsive to activation of the plural key switches for selectively coupling different ones of the plural output signals to the visual indicator means so only one of the output signals is supplied to the indicator means at a time.

32. The apparatus of claim 31 wherein the first signal deriving means includes means for monitoring the number of heart beats of the subject.

33. The apparatus of claim 32 wherein the means for monitoring the number of heart beats includes electrodes adapted to be on the subject for deriving an electrocardiogram signal.

34. The apparatus of claim 33 wherein the means for monitoring further includes means for detecting r pulses of the electrocardiogram signal to the exclusion of other pulses of the electrocardiogram signal.

35. The apparatus of claim 34 wherein the means for detecting r pulses includes a band pass filter for passing the r pulses and a clamping circuit for peaks of the r pulses.

36. The apparatus of claim 33 or 34 further including full wave rectifier means for the r pulses so that r pulses of only one polarity are applied to the clamping means regardless of the connections of the electrodes to the r pulse detecting means.

37. The apparatus of claim 33 or 34 further including means for preventing derivation of the first signal in response to a pair of adjacent detected r pulses occurring in less than a predetermined interval which is less than the possible period between adjacent beats of a heart.

38. The apparatus of claim 33 or 34 or 35 wherein three electrodes are provided on the subject, each electrode being associated with a lead wire, shield means for the lead wires, said three lead wires and shield means being connected to three sets of input terminals of an electronic instrument housing, each set of input terminals including a grounded terminal connected to the shield means and a signal input terminal, one of said signal input terminals being connected to a DC reference level, differential amplifier means responsive to voltages at the other two signal input terminals, and means for referencing the differential amplifier means to the reference level to provide common mode rejection for voltages generated by said electrodes.

39. The apparatus of claim 31 further including an aural indicator, and means for pulsing the aural indicator in response to each heart beat, said pulsing means being activated when the computer means is responsive to at least a predetermined number of beats in a predetermined interval, as indicated by the first and timing signals.

40. The apparatus of claim 32 wherein the means for monitoring the number of heart beats include means for detecting absorption changes of optical energy in a vein of the subject in response to pressure waves resulting from beats of the heart.

41. The apparatus of claim 40 wherein the detecting means includes an infra red optical energy source and an infra red detector responsive to optical energy from the infra red source reflected from the vessel.

42. The apparatus of claim 41 wherein the infra red source and infra red detector are mounted on a support adapted to be mounted on a fingertip of the subject.

43. The apparatus of claim 42 wherein the infra red source and infra red detector are mounted on a support adapted to be mounted on a brachialis muscle of the subject.

44. The apparatus of claim 31 wherein the first signal deriving means includes means for monitoring the number of heart beats of the subject, the keyboard deriving signals indicative of the sex, age, rest heart rate, and weight of the subject, said computer means being responsive to the signals for deriving the physical activity signal as a function of the maximum oxygen uptake of the subject.

45. The apparatus of claim 31 wherein the first signal deriving means includes means for monitoring the number of heart beats of the subject, the keyboard deriving signals indicative of the sex, age, rest heart rate, and weight of the subject, said computer means being responsive to the signals for deriving the physical activity signal as a function of the calorie consumption of the subject, one of said keys being for calorie consumption.

46. The apparatus of claim 31 wherein the first signal deriving means includes means for monitoring the number of heart beats of the subject, the keyboard deriving signals indicative of the sex, age, rest heart rate, and weight of the subject, said computer means being responsive to the signals for deriving the first and second physical activity signals respectively representing calorie consumption of the subject and the time rate at which the subject performs an aerobic exercise associated with movement of the limb, first and second of said keys being for calorie consumption and time rate.

47. Portable apparatus for testing the physical condition of a subject performing an aerobic exercise involving motion of a limb of the subject comprising means adapted to be mounted on the subject for monitoring and deriving a first signal indicative of heart activity of the subject, means for deriving a second signal indicative of distance traversed by the subject during testing, a housing adapted to be mounted on the subject, said housing including: (a) input means for deriving at least one signal indicative of a predetermined constant physiologically relevant, parameter of the subject, (b) a clock source for deriving a timing signal during testing of the subject, (c) computer means responsive to the first, second, predetermined physiologically relevant parameter and timing signals for calculating the magnitude of a signal indicative of physical activity of the subject being tested in response to the values of said first and second signals, said physiologically relevant parameter and timing signals, and (d) indicator means responsive to the physical activity signal.

48. Apparatus for testing the physical condition of a subject performing an aerobic exercise involving motion of a limb comprising means adapted to be mounted on the subject for monitoring and deriving a first signal indicative of heart activity of the subject, means for deriving a second signal indicative of distance traversed by the subject during testing, a portable electronic instrument housing adapted to be mounted on the subject, means for coupling said first signal to terminals on the instrument housing, said housing including: (a) a keyboard for enabling signals to be derived indicative of numerical quantities associated with a plurality of physiologically relevant, predetermined constant value parameters of the subject, (b) a clock source for deriving timing signals, (c) digital computer means responsive to the first, second, timing and keyboard signals for deriving plural digital output signals indicative of different physical activities of the tested subject, at least some of the digital output signals being calculated by the computer means in response to the values of said first and second signals, and said physiologically relevant parameter signal and said timing signal, (d) visual digital indicator means, (e) plural key switches, each associated with a different one of the physical activities, and (f) means responsive to activation of the plural key switches for selectively coupling different ones of the plural output signals to the visual indicator means so only one of the output signals is supplied to the indicator means at a time.

49. The apparatus of claims 47 or 48 wherein the first signal deriving means includes means for monitoring the number of heart beats of the subject.

50. Apparatus for testing the physical condition of a subject comprising means adapted to be physically coupled to the subject for monitoring and deriving a first signal proportional to a heart beat rate of the subject, means for deriving a second signal proportional to distance traversed by the subject during testing, input means for deriving at least one signal indicative of a predetermined physiologically relevant parameter of the subject, said parameter having a constant, predetermined value for the particular subject, a clock source for deriving a timing signal during testing of the subject, and computer means responsive to the first, second, predetermined physiologically relevant parameter and timing signals for calculating the magnitude of a signal indicative of physical activity of the subject being tested in response to the values of said first and second signals, said physiologically relevant parameter, and said timing signal, and indicator means responsive to the physical activity signal for displaying the magnitude of the physical activity signal.

51. The apparatus of claim 1, 23 or 50 wherein the first signal deriving means includes means for monitoring the number of heart beats of the subject, the input means deriving signals indicative of the sex, age, rest heart rate, and weight of the subject, said computer means being responsive to all of the signals for deriving the physical activity signal as a function of the maximum oxygen uptake of the subject.

52. The apparatus of claim 1, 23 or 48 wherein the first signal deriving means includes means for monitoring the number of heart beats of the subject, the input means deriving signals indicative of the sex, age, rest heart rate, and weight of the subject, said computer means being responsive to the signals for deriving the physical activity signal as a function of the calorie consumption of the subject.

53. The apparatus of claim 1, 23 or 48 wherein the first signal deriving means includes means for monitoring the number of heart beats of the subject, the input means deriving signals indicative of the sex, age, rest heart rate, and weight of the subject, said computer means being responsive to all of the signals for deriving the first and second physical activity signals respectively representing calorie consumption of the subject and the time rate at which the subject performs an aerobic exercise associated with movement of the limb.

* * * * *